US011366122B2

(12) United States Patent
Ha et al.

(10) Patent No.: US 11,366,122 B2
(45) Date of Patent: Jun. 21, 2022

(54) PICOLITER DROPLET SAMPLE PROCESSING AND DEPOSITION FOR MASS SPECTROMETRY

(71) Applicant: The Regents of the University of California, Oakland, CA (US)

(72) Inventors: Noel Ha, El Cerrito, CA (US); Markus de Raad, Berkeley, CA (US); Trent R. Northen, Walnut Creek, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 17/062,609

(22) Filed: Oct. 4, 2020

(65) Prior Publication Data
US 2021/0102954 A1  Apr. 8, 2021

Related U.S. Application Data

(60) Provisional application No. 62/911,165, filed on Oct. 4, 2019.

(51) Int. Cl.
*G01N 33/68* (2006.01)
*H01J 49/04* (2006.01)
*H01J 49/00* (2006.01)

(52) U.S. Cl.
CPC ...... *G01N 33/6851* (2013.01); *H01J 49/0004* (2013.01); *H01J 49/0418* (2013.01)

(58) Field of Classification Search
CPC .............. G01N 33/6851; H01J 49/0004; H01J 49/0418
See application file for complete search history.

(56) References Cited

U.S. PATENT DOCUMENTS

| 10,240,180 | B2 | 3/2019 | Northen et al. |
| 2008/0128608 | A1 | 6/2008 | Northen et al. |
| 2017/0348665 | A1 | 12/2017 | Duncombe et al. |
| 2018/0254177 | A1 | 9/2018 | Gao et al. |
| 2018/0269052 | A1 | 9/2018 | Gao et al. |

FOREIGN PATENT DOCUMENTS

WO    WO2016149661    9/2016

OTHER PUBLICATIONS

De Raad et al., "High-throughput platforms for metabolomics," Current Opinion in Chemical Biology 2016, 30, 7-13.
Deng et al., "Encoding substrates with mass tags to resolve stereospecific reactions using Nimzyme," Rapid Communications in Mass Spectrometry 2012, 26, 611-615.

(Continued)

*Primary Examiner* — Nicole M Ippolito
*Assistant Examiner* — Hanway Chang
(74) *Attorney, Agent, or Firm* — Sheppard, Mullin, Richter & Hampton LLP

(57) ABSTRACT

Disclosed herein include systems, devices, and methods for droplet deposition for mass spectrometry. In some embodiments, a microfluidic device comprising wells is reversibly sealed to a mass spectrometry surface and used to deposit contents of droplets (e.g., enzymes and substrates), or products thereof, onto the mass spectrometry surface. The contents of droplets can be analyzed by laser desorption/ionization to, for example, identify a substrate of an enzyme or an enzyme capable of catalyzing a substrate to a product.

20 Claims, 18 Drawing Sheets

(56) References Cited

OTHER PUBLICATIONS

Ha et al., "Massive Screening of Metabolites Using Picoliter Droplet Array with Nanostructure-Initiator Mass Spectrometry," The 23rd International Conference on Miniaturized Systems for Chemistry and Life Sciences, Oct. 31, 2019 9:35am, in 2 pages.

Kulesa et al., "Combinatorial drug discovery in nanoliter droplets," PNAS 2018, 115(26), 6685-6690.

Northen et al., "Clathrate nanostructures for mass spectrometry," Nature 2007, 449, 1033-1036.

Northen et al., "A nanostructure-initiator mass spectrometry-based enzyme activity assay," PNAS 2008, 105(10), 3678-3683.

Woo et al., "Nanostructure-initiator mass spectrometry: a protocol for preparing and applying NIMS surfaces for high-sensitivity mass analysis," Nature Protocols 2008, 3(8), 1341-1349.

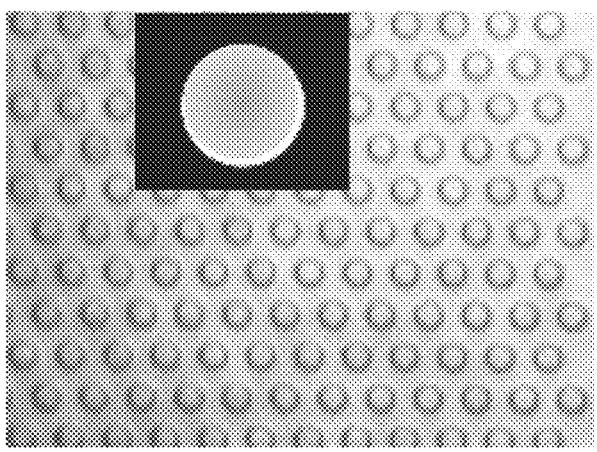
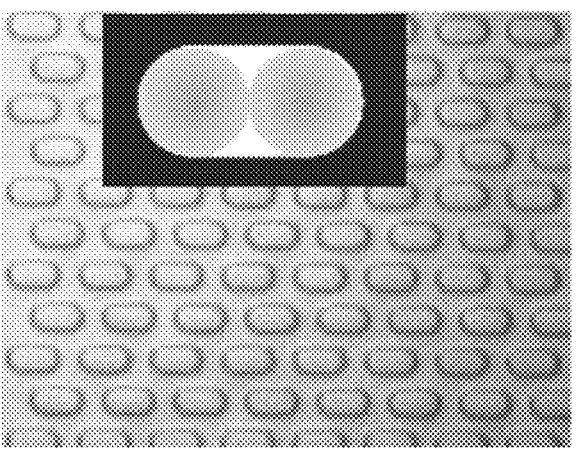
FIG. 4A  FIG. 4B
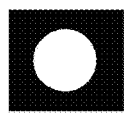 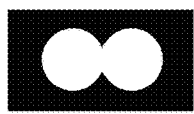 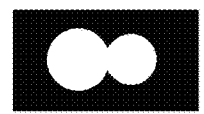
FIG. 4C  FIG. 4D  FIG. 4E
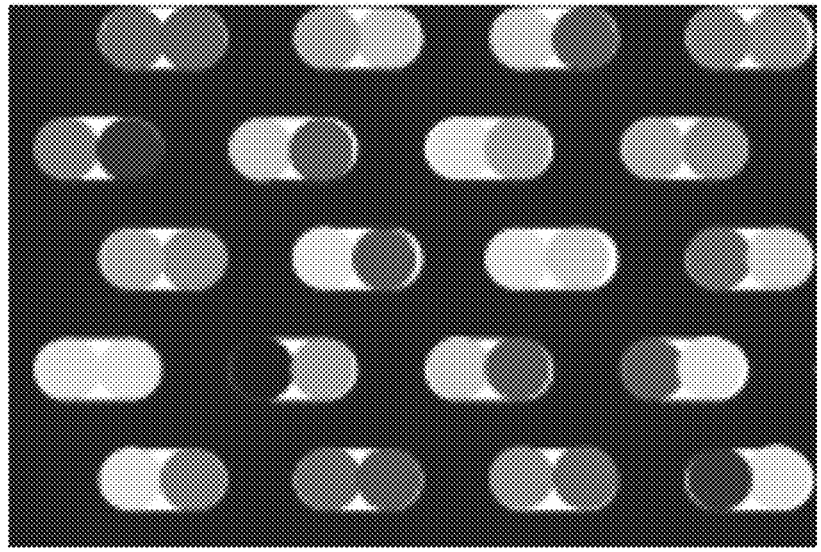
FIG. 4F
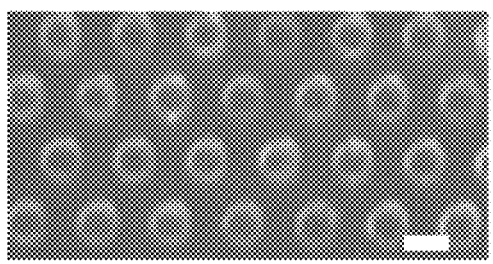
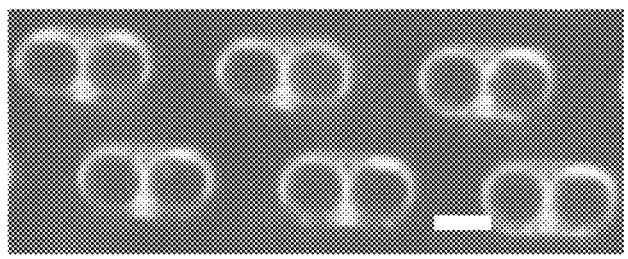
FIG. 4G  FIG. 4H

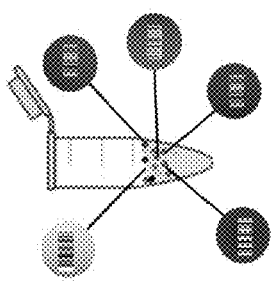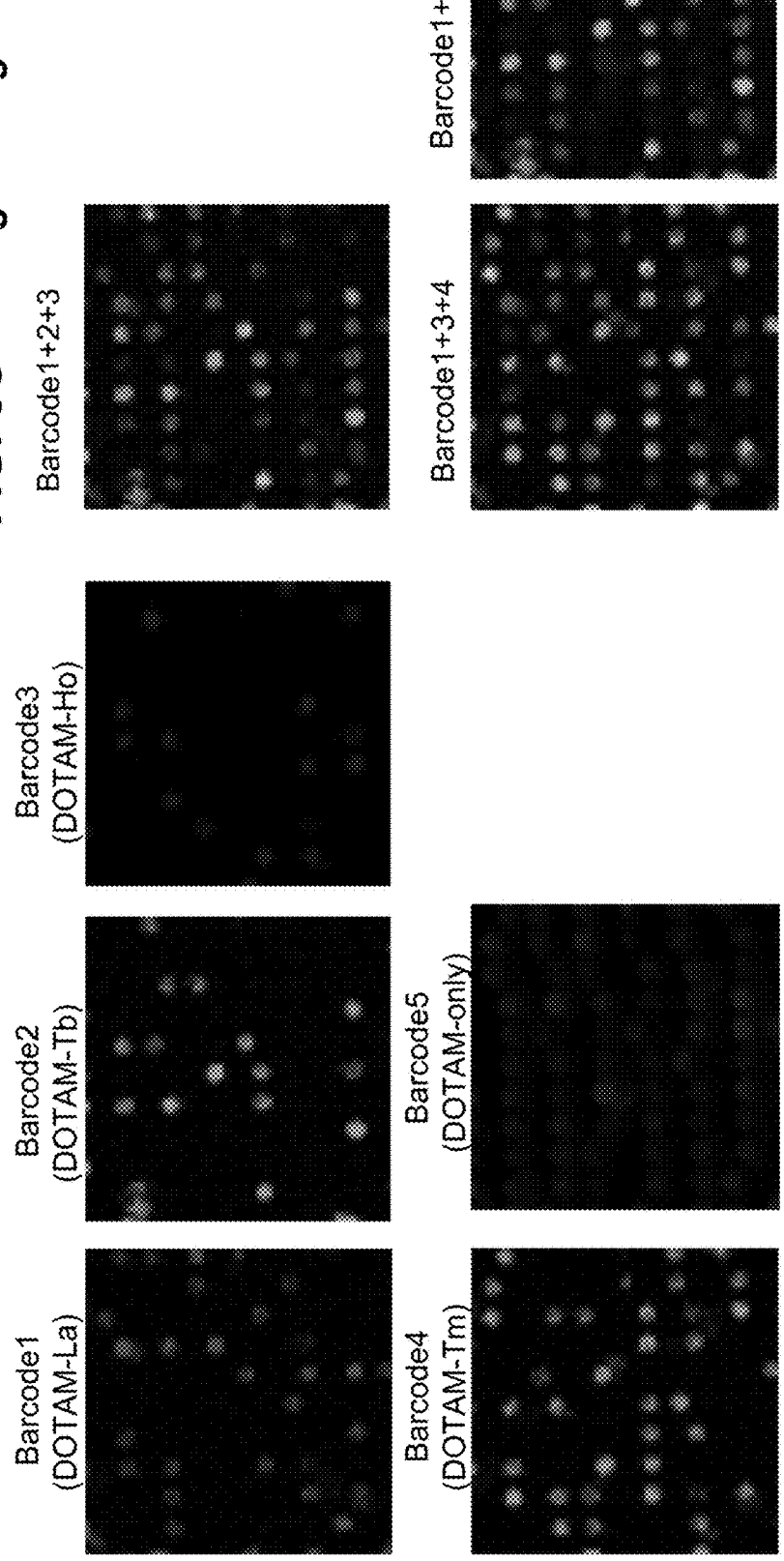

PICOLITER DROPLET SAMPLE PROCESSING AND DEPOSITION FOR MASS SPECTROMETRY

CROSS-REFERENCE TO RELATED APPLICATIONS

This application claims the benefit of priority to U.S. Provisional Patent Application No. 62/911,165, filed Oct. 4, 2019, the content of which is incorporated herein by reference in its entirety.

STATEMENT REGARDING FEDERALLY SPONSORED R&D

This invention was made with government support under grant no. DE-AC02-05CH11231 awarded by U.S. Department of Energy, Office of Science, Office of Biological and Environmental Research. The government has certain rights in the invention.

BACKGROUND

Field

The present disclosure relates generally to the field of mass spectrometry, for example sample deposition for mass spectrometry analysis.

Description of the Related Art

Enzymes are essential to synthetic biology and biofuel production as well as in drug metabolism. However, only a relatively small fraction of predicted enzymes has been biochemically characterized. In additional to all naturally occurring enzymes, millions of unknown enzymes can be produced by mutagenesis such as error-prone polymerase chain reaction (PCR). Combinatorial screening of massive scale enzyme libraries through metabolite detection has the potential to discover and analyze new enzymes and multi-step metabolic pathways. To date, electrospray ionization has been widely coupled with microfluidics for online mass spectrometry (MS) analysis, but often struggles with decreasing sensitivity over many thousands of consecutive measurements. The most common method of microscale sample droplets deposition on the MS surface is via an acoustic printing. However, the minimum required sample volume is typically larger than a nanoliter, and more importantly acoustic printing cannot pair or merge multiple droplets on the MS surface once printed.

SUMMARY

Disclosed herein include embodiments of a method for screening one or more analytes. In some embodiments, the method comprises: distributing droplets from a first plurality of droplets each potentially comprising one or more first analytes onto an array of wells, thereby loading into one, at least one, or each, of the wells of the array one or more distributed droplets. The method can comprise: contacting a mass spectrometry (MS) surface of a mass spectrometry chip with a well-opening surface of the array of wells, thereby depositing the one or more first analytes, if any, in the one, at least one, or each, of the plurality of wells onto a location on the mass spectrometry surface corresponding to the well. The method can comprise: obtaining a mass spectrum of the one or more first analytes, if any, deposited onto one, at least one, or each, of the locations on the mass spectrometry surface from a droplet of the first plurality of droplets. The method can comprise: determining a presence, or an absence, of a first analyte of the one or more analytes in one, at least one, or each, of the droplets from the plurality of first droplets using a presence, or an absence, of a first peak corresponding to the first analyte in a mass spectrum of the mass spectra obtained from a location of the locations on the mass spectrometry surface onto which a content of the droplet is deposited. The method can comprise: for one, at least one, or each of the mass spectra obtained, determining a presence, or an absence, of a first analyte of the one or more analytes in one, at least one, or each, of the droplets from the plurality of first droplets using a presence, or an absence, of a first peak corresponding to the first analyte in the mass spectrum of the mass spectra obtained from a location of the locations on the mass spectrometry surface onto which a content of the droplet is deposited.

In some embodiments, one, at least one, or each, of the wells of the array is sized and/or shaped to capture one or more of the droplets from the first plurality of droplets (such as 1, 2, 3, 4, 5, 6, 7, 8, 9, 10, or more droplets).

In some embodiments, the method comprises generating the first plurality of droplets each comprising the one or more first analytes. The method can comprise generating the first plurality of droplets comprises generating the first plurality of droplets from a library of samples. The library of samples can comprise a library of first analytes. The library of first analytes can comprise a library of enzymes, a library of drugs, a library of metabolites, a library of antibiotics, or a combination thereof. Generating the first plurality of droplets can comprise generating a droplet of the first plurality of droplets from a sample. The method can comprise determining a presence, or an absence, of the first analyte in the sample using the presence, or the absence, of the first analyte determined. The sample can comprise a clinical sample, a soil sample, an air sample, an environmental sample, a cell culture sample, a bone marrow sample, a rainfall sample, a fallout sample, a sewage sample, a ground water sample, an abrasion sample, an archaeological sample, a food sample, a blood sample, a serum sample, a plasma sample, a urine sample, a stool sample, a semen sample, a lymphatic fluid sample, a cerebrospinal fluid sample, a nasopharyngeal wash sample, a sputum sample, a mouth swab sample, a throat swab sample, a nasal swab sample, a bronchoalveolar lavage sample, a bronchial secretion sample, a milk sample, an amniotic fluid sample, a biopsy sample, a cancer sample, a tumor sample, a tissue sample, a cell sample, a cell culture sample, a cell lysate sample, a virus culture sample, a nail sample, a hair sample, a skin sample, a forensic sample, an infection sample, a nosocomial infection sample, a production sample, a drug preparation sample, a biological molecule production sample, a protein preparation sample, a lipid preparation sample, a carbohydrate preparation sample, a space sample, an extraterrestrial sample or a combination thereof.

In some embodiments, the one or more first analytes comprise a protein, an enzyme, an antibody, an immunogen, an antigen, a drug, a metabolite, an antibiotic, a nucleic acid, a lipid, a carbohydrate, a cell, a microbial cell, or a combination thereof. In some embodiments, at least two of the droplets from the first plurality of droplets comprises the one or more first analytes in different concentrations, or comprise different buffer conditions. At least two of the droplets from the first plurality of droplets can comprise different one or more first analytes.

In some embodiments, determining the presence, or the absence, of the first analyte comprises determining an increase, or a decrease, of the first analyte in one, at least one, or each, of the droplets from the plurality of first droplets using an increase, or a decrease, of the first peak corresponding to the first analyte in the mass spectrum obtained from the location on the mass spectrometry surface onto which the content of the droplet is deposited. The method can comprise determining a stability of the one or more first analytes based on the presence, the absence, the increase in, or the decrease in, the first peak corresponding to the first analyte in the mass spectrum.

Disclosed herein include embodiments of a method for sample deposition on a mass spectrometry surface. In some embodiments, the method comprises: (a) generating a first plurality of droplets each comprising one or more first analytes. The method can comprise: (b) distributing droplets from the first plurality of droplets onto an array of wells in a microfluidic device. One, at least one, or each, of the wells of the array can be sized and/or shaped to capture one or more of the droplets from the first plurality of droplets (such as 1, 2, 3, 4, 5, 6, 7, 8, 9, 10, or more droplets). The method can comprise: (c) contacting a mass spectrometry (MS) surface of a MS chip with the well-opening surface of the array of wells comprising the distributed droplets from the first plurality of droplets, thereby depositing the one or more first analytes from the first plurality of droplets, or products thereof, onto the mass spectrometry surface.

In some embodiments, the method comprises: (d) generating a second plurality of droplets each comprising one or more second analytes; and (e) distributing droplets from the second plurality of droplets onto the array of wells. In some embodiments, the method comprises: (d) generating a 3rd plurality, a 4th plurality, a fifth plurality, . . . , and a nth plurality of droplets each comprising one or more 3rd, 4th, 5th, . . . , or nth analytes, respectively; and (e) distributing droplets from the 3rd plurality, the 4th plurality, the 5th plurality, . . . , and/or the nth plurality of droplets onto the array of wells (such as into wells of the array of wells). Contacting the mass spectrometry surface with the well-opening surface of the array of wells can comprise contacting the mass spectrometry surface with the well-opening surface of the array of wells comprising the droplets from the first plurality of droplets and the droplets from the second (or 3rd, 4th, etc.) plurality of droplets, thereby depositing the one or more first analytes from the first plurality of droplets, or products thereof, and the one or more second (or 3rd, 4th, etc.) analytes from the second (or 3rd, 4th, etc.) plurality of droplets, or products thereof, onto the mass spectrometry surface.

In some embodiments, the method comprises: generating a mixture of the first plurality of droplets and the second plurality of droplets (and the 3rd plurality, the 4th plurality, the fifth plurality, . . . , and/or the nth plurality of droplets), wherein the droplets from the first plurality of droplets and the droplets form the second plurality of droplets are loaded into the array of wells together by distributing onto the array of wells the mixture of the first plurality of droplets and the second plurality of droplets. In some embodiments, the droplets from the first plurality of droplets and the droplets form the second plurality of droplets are loaded into wells of the array of wells sequentially.

In some embodiments, the array of wells is positioned with the well-opening surface facing down. The mass spectrometry chip can be positioned with mass spectrometry surface facing up. In some embodiments, the array of wells is positioned with the well-opening surface facing up. The mass spectrometry chip can be positioned with mass spectrometry surface facing down.

In some embodiments, distributing the droplets from the first plurality of droplets onto the array of wells comprises flowing the first plurality of droplets in a carrier fluid through a channel formed by a space between the well-opening surface of the array of wells and the mass spectrometry surface. The carrier fluid can be an oil and/or a non-ionic surfactant. In some embodiments, distributing the droplets from the first plurality of droplets onto the array of wells comprises distributing the droplets from the first plurality of droplets into wells of the array.

In some embodiments, distributing the droplets from the second plurality of droplets onto the array of wells comprises flowing the second plurality of droplets in a carrier fluid through the channel formed by the space between the well-opening surface of the array of wells and the mass spectrometry surface. Distributing the droplets from the second plurality of droplets onto the array of wells can comprise distributing the droplets from the second plurality of droplets into wells of the array.

In some embodiments, one or more of the wells in the array of wells are each sized and/or shaped to capture two or more of the droplets from the first plurality of droplets or two or more droplets from the second plurality of droplets. In some embodiments, one, at least one, or each, of the wells of the array is sized and/or shaped to capture (i) at most one of the droplets from the first plurality of droplets, and (ii) at most one of the droplets from the second plurality of droplets when the droplet from the first plurality of droplets is captured in the well of the array. The droplets from the first plurality of droplets can be larger than the droplets from the second plurality of droplets. Distributing the droplets from the first plurality of droplets can occur before distributing the droplets from the second plurality of droplets, thereby one, at least one, or each, of the wells of the array comprises: (i) none of the droplets from the first plurality of droplets and none of the droplets from the second plurality of droplets, (ii) one of the droplets from the first plurality of droplets and none of the droplets from the second plurality of droplets, (iii) one of the droplets from the first plurality of droplets and one of the droplets from the second plurality of droplets, or (iv) at least one of the droplets from the second plurality of droplets.

In some embodiments, distributing the droplets from the first and second plurality of droplets onto the array of wells comprises introducing (e.g., loading) both one droplet from the first plurality of droplets and one droplet from the second plurality of droplets into at least one well of the array of wells. In some embodiments, distributing droplets from the first and/or second plurality of droplets comprises randomly distributing the droplets to the array of wells.

In some embodiments, at least 50%, at least 75%, or at least 90% of the wells of the array of wells each comprises both one droplet from the first plurality of droplets and one droplet from the second plurality of droplets.

In some embodiments, the droplets from the first plurality of droplets, the droplets from the second plurality of droplets, or both, have an average diameter of about 10 µm to about 400 µm, about 20 µm to about 200 µm, or about 70 µm to about 150 µm. A dimension of each of more than 50%, more than 75%, or more than 95% of the wells in the array of wells can be about 20 µm to about 410 µm, 30 µm to about 210 µm, or about 80 µm to about 160 µm. A dimension of each of more than 50%, more than 75%, or more than 95% of the wells in the array of wells can be about 150 µm to about 310 μm. The dimension can be a width, a height, a depth, or a combination thereof, of the well.

In some embodiments, the method comprises merging the one droplet from the first plurality of droplets and the one droplet from the second plurality of droplets in the well where the two droplets are introduced into. Merging the one droplet from the first plurality of droplets and the one droplet from the second plurality of droplets in the well where the two droplets are introduced into can comprise applying a voltage. Merging the one droplet from the first plurality of droplets and the one droplet from the second plurality of droplets in the well where the two droplets are introduced into can comprise applying a voltage to the array of wells. The side of the array of wells opposite of the well-opening surface of the array of wells can be in contact with an additional layer (e.g., a glass layer). Merging the one droplet from the first plurality of droplets and the one droplet from the second plurality of droplets in the well where the two droplets are introduced into can comprise applying a voltage to the additional layer. Merging the one droplet from the first plurality of droplets and the one droplet from the second plurality of droplets in the well where the two droplets are introduced into can comprise applying a voltage to the mass spectrometry chip. If one of the droplets being merged in a well comprises an enzyme and another of the droplets being merged comprises a substrate of the enzyme, after the droplets are merged, the enzyme can catalyze the substrate into a product. The peak corresponding to the substrate in the mass spectrum from a position of the MS surface corresponding to the well can be absent or smaller. A substrate of the enzyme can be identified. Alternatively, or additionally, the peak corresponding to the product in the mass spectrum from a position of the MS surface corresponding to the well can be present. Alternatively, or additionally, an enzyme capable of catalyzing the substrate into a product can be identified as described herein (e.g., using an optical label, chemical label, nucleotide label, or peptide label in the droplet comprising the enzyme and/or associated with the enzyme).

In some embodiments, contacting the well-opening surface of the array of wells with the mass spectrometry surface comprises sealing the well-opening surface of the array of wells with the mass spectrometry surface via a reversible sealing mechanism. The reversible sealing mechanism can comprise a top clamp located above the array of wells and a bottom clamp on which the mass spectrometry chip is placed. The top clamp can be a clamping plate located above the side of the array of wells opposite of the well-opening surface of the array of wells, and the bottom clamp can be a clamping plate located below a side of the mass spectrometry chip opposite of the mass spectrometry surface.

In some embodiments, the one or more first analytes from the first plurality of droplets, the one or more second analytes from the second plurality of droplets, or both, comprise a protein, a polypeptide, a peptide, a nucleic acid, a lipid, a carbohydrate, a small molecule drug, a cell, or any combination thereof. In some embodiments, the one or more first analytes from the first plurality of droplets, the one or more second analytes from the second plurality of droplets, or both, comprise an enzyme, a dye, an enzymatic substrate, a metabolite, or any combination thereof. In some embodiments, the one or more first analytes from the first plurality of droplets comprise an enzyme, and the one or more second analytes from the second plurality of droplets comprise a possible enzymatic substrate of the enzyme, or the one or more second analytes from the second plurality of droplets comprise an enzymatic substrate and the one or more first analytes from the first plurality of droplets comprise an enzyme being screened for a capability of converting the enzymatic substrate into a product. In some embodiments, the substrate is a drug, and the enzyme is capable of metabolizing the drug to the product.

In some embodiments, the droplets from the first and/or second plurality of droplets rise or sink via buoyancy from the space between the well-opening surface of the array of wells and the mass spectrometry surface into the wells. In some embodiments, the droplets from the first plurality of droplets, the droplets from the second plurality of droplets, or both are in a solvent-in-oil emulsion. The oil in the solvent-in-oil emulsion can be a fluorinated oil. The solvent in the solvent-in-oil emulsion can be water, a buffer solution, a salt solution, an organic solvent, or any combination thereof. In some embodiments, the method comprises evaporating the solvent, the oil, and/or the carrier fluid from the mass spectrometry surface.

In some embodiments, the droplets from the first plurality of droplets, the droplets from the second plurality of droplets, or both comprise a detectable barcode that identifies the one or more first or second analytes in a given droplet. The detectable barcode can comprise an optically detectable label, a label detectable by mass spectrometry, or both. The optically detectable label can be a fluorophore. The label detectable by mass spectrometry can be a lanthanide-chelator complex. The detectable barcode can be selected from a set of at least 20 distinct barcodes.

In some embodiments, the method comprises identifying the one or more first or second analytes, or products thereof, deposited onto the mass spectrometry surface using mass spectrometry. The mass spectrometry can be laser desorption/ionization MS. The laser desorption/ionization MS can be nanostructure-initiator mass spectrometry (NIMS), desorption/ionization on silicon (DIOS) MS, nanowire-assisted laser desorption/ionization (NALDI) MS, insulator nanostructure desorption ionization (INDI) MS, nanopost array laser desorption ionization (NAPA) MS, matrix-assisted laser desorption/ionization (MALDI) MS, surface-assisted laser desorption/ionization (SALDI) MS, surface-enhanced laser desorption/ionization (SELDI) MS, or a combination thereof.

Disclosed herein include embodiments of a method for screening one or more reactions. In some embodiments, the method comprises: (a) generating a first plurality of droplets each comprising one or more potential reaction partners of an analyte and a second plurality of droplets each comprising the analyte. In some embodiments, the method comprises: (a) generating a first plurality of droplets each comprising an analyte and a second plurality of droplets each comprising one or more potential reaction partners of the analyte. The method can comprise: (b) distributing droplets from the first plurality of droplets and the second plurality of droplets onto an array of wells in a microfluidic device, thereby loading into one, at least one, or each, of the wells of the array zero, one, or two (or more, such as 3, 4, 5, 6, 7, 8, 9, 10, or more) distributed droplets. The method can comprise: (c) contacting a mass spectrometry (MS) surface of a mass spectrometry chip with a well-opening surface of the array of wells, thereby depositing (i) the one or more potential reaction partners, or products thereof, if any, and (ii) the analyte, if any, from the zero, one, or two (or more, such as 3, 4, 5, 6, 7, 8, 9, 10, or more) distributed droplets in the one, at least one, or each, of the plurality of wells onto a location on the mass spectrometry surface corresponding to the well. The method can comprise: (d) obtaining a mass spectrum of the one or more potential reaction partners, or products thereof, if any, and the analyte, or a product thereof, if any, deposited onto one, at least one, or each, of the locations on the mass spectrometry surface. The method can comprise: (e) determining a potential reaction partner is a reaction partner of the analyte using an absence of, or a decrease in, a first peak corresponding to the substrate, a presence of, or an increase in, the first peak corresponding to the substrate, an absence of, or a decrease in, a second peak corresponding to the analyte, and/or a presence of, or an increase in, the second peak corresponding to the analyte in a mass spectrum of the mass spectra obtained. The method can comprise: for one, at least one, or each of the mass spectra obtained, (e) determining a potential reaction partner is a reaction partner of the analyte using an absence of, or a decrease in, a first peak corresponding to the substrate, a presence of, or an increase in, the first peak corresponding to the substrate, an absence of, or a decrease in, a second peak corresponding to the analyte, and/or a presence of, or an increase in, the second peak corresponding to the analyte in the mass spectrum of the mass spectra obtained.

In some embodiments, the analyte comprises one or more of proteins, nucleic acids, lipids, carbohydrates, and cells, or a combination thereof. The one or more potential reaction partners can comprise one or more of proteins, nucleic acids, lipids, carbohydrates, cells, or a combination thereof. The analyte and/or the one or more potential reaction partners can comprise drugs, enzymes, antibodies, immunogens, antigens, metabolites, antibiotics, microbial cells, or a combination thereof. The one or more potential reaction partners of the analyte can comprise one or more potential substrates of an enzyme, and wherein the analyte comprises an enzyme. The enzyme can be capable of catalyzing one substrate of the one or more potential substrates to a product. The one or more potential reaction partners of the analyte can comprise one or more enzymes potentially capable of catalyzing a substrate to a product, and wherein the analyte comprises the substrate. One enzyme of the one or more enzymes potentially capable of catalyzing the substrate to the product can be capable of catalyzing the substrate to the product. The substrate can be a drug, and the enzyme can be capable of metabolizing the drug to the product.

In some embodiments, at least two of the droplets from the first plurality of droplets comprises one potential reaction partner in different concentrations, or comprise different buffer conditions. At least two of the droplets from the second plurality of droplets comprise the analyte in different concentrations or comprise different buffer conditions.

Disclosed herein include embodiments of a method for screening for an enzyme substrate. In some embodiments, the method comprises: (a) generating a first plurality of droplets each comprising one or more potential substrates of an enzyme and a second plurality of droplets each comprising the enzyme. The method can comprise: (b) distributing droplets from the first plurality of droplets and the second plurality of droplets onto an array of wells in a microfluidic device. One, at least one, or each, of the wells of the array can be sized and/or shaped to capture (i) one of the droplets from the first plurality of droplets and (ii) one of the droplets from the second plurality of droplets, thereby loading into one, at least one, or each, of the wells of the array zero, one, or two (or more, such as 3, 4, 5, 6, 7, 8, 9, 10, or more) distributed droplets. The method can comprise: (c) contacting a mass spectrometry (MS) surface of a mass spectrometry chip with a well-opening surface of the array of wells, thereby depositing (i) the one or more potential substrates, or products thereof, if any, and (ii) the enzyme, if any, from the zero, one, or two (or more, such as 3, 4, 5, 6, 7, 8, 9, 10, or more) distributed droplets in the one, at least one, or each, of the plurality of wells onto a location on the mass spectrometry surface corresponding to the well. The method can comprise: (d) obtaining a mass spectrum of the one or more potential substrates, or products thereof, if any, and the enzyme, if any, deposited onto one, at least one, or each, of the locations on the mass spectrometry surface. The method can comprise: (e) determining a potential substrate is a substrate of the enzyme using an absence of, or a decrease in, a first peak corresponding to the substrate, a presence of, or an increase in, a second peak corresponding to a product (or second peaks corresponding to products) catalyzed from the substrate by the enzyme, and/or a third peak corresponding to the enzyme (e.g., the enzyme, or a barcode or a label identifying the enzyme) in a mass spectrum of the mass spectra obtained.

Disclosed herein include embodiments of a method for screening for an enzyme capable of catalyzing a substrate to a product. In some embodiments, the method comprises: (a) generating a first plurality of droplets each comprising an identical substrate and a second plurality of droplets each comprising one or more potential enzymes capable of catalyzing the substrate to a product. The method can comprise: (b) distributing droplets from the first plurality of droplets and the second plurality of droplets onto an array of wells in a microfluidic device. One, at least one, or each, of the wells of the array can be sized and/or shaped to capture (i) one of the droplets from the first plurality of droplets and (ii) one of the droplets from the second plurality of droplets, thereby loading into one, at least one, or each, of the wells of the array zero, one, or two (or more, such as 3, 4, 5, 6, 7, 8, 9, 10, or more) distributed droplets. The method can comprise: (c) contacting a mass spectrometry (MS) surface of a mass spectrometry chip with a well-opening surface of the array of wells, thereby depositing (i) the substrate, or one or more products thereof, if any, and (ii) the zero, one, or two (or more, such as 3, 4, 5, 6, 7, 8, 9, 10, or more) potential enzymes from the zero, one, or two (or more, such as 3, 4, 5, 6, 7, 8, 9, 10, or more) distributed droplets in the one, at least one, or each, of the plurality of wells onto a location on the mass spectrometry surface corresponding to the well. The method can comprise: (d) obtaining a mass spectrum of the substrate, or one or more products thereof, if any, and the zero, one, or two (or more, such as 3, 4, 5, 6, 7, 8, 9, 10, or more) enzymes deposited onto one, at least one, or each, of the locations on the mass spectrometry surface. The method can comprise: (e) determining a potential enzyme is an enzyme capable of catalyzing the substrate to a product (or products) using an absence of, or a decrease in, a first peak corresponding to the substrate, a presence of, or an increase in, a second peak corresponding to the product (or second peaks corresponding to the products), and/or a third peak corresponding to the enzyme (e.g., the enzyme, or a barcode or a label identifying the enzyme) capable of catalyzing the substrate to the product in a mass spectrum of the mass spectra obtained.

Disclosed herein include embodiments of a method for screening an enzyme and a substrate of the enzyme in a reaction. In some embodiments, the method comprises: (a) generating a first plurality of droplets each comprising one or more first analytes (e.g., a substrate, or potential substrates) and a second plurality of droplets each comprising one or more second analytes (e.g., potential enzymes capable of catalyzing the substrate into a product, or an enzyme). The method can comprise: (b) distributing droplets from the first plurality of droplets and the second plurality of droplets onto an array of wells in a microfluidic device. One, at least one, or each, of the wells of the array can be sized and/or shaped to capture (i) one of the droplets from the first plurality of droplets and (ii) one of the droplets from the second plurality of droplets, thereby loading into one, at least one, or each, of the wells of the array zero, one, or two (or more, such as 3, 4, 5, 6, 7, 8, 9, 10, or more) distributed droplets. The method can comprise: (c) contacting a mass spectrometry (MS) surface of a mass spectrometry chip with a well-opening surface of the array of wells, thereby depositing (i) the one or more first analytes, or products thereof, if any, and (ii) the one or more second analytes, or products thereof, if any, from the zero, one, or two (or more, such as 3, 4, 5, 6, 7, 8, 9, 10, or more) distributed droplets in the one, at least one, or each, of the plurality of wells onto a location on the mass spectrometry surface corresponding to the well. The method can comprise: (d) obtaining a mass spectrum of the one or more first analytes, or products thereof, if any, and the one or more second analytes, or products thereof, if any, deposited onto one, at least one, or each, of the locations on the mass spectrometry surface. The method can comprise: (e) determining a first analyte and a second analyte are components of a reaction using a first peak, or absence thereof, corresponding to the first analyte, and/or a second peak, or absence thereof, corresponding to the second analyte in a mass spectrum of the mass spectra obtained. In some embodiments, one, at least one, or each, of the first plurality of droplets each comprises an identical first analyte, and two droplets of the second plurality of droplets comprise different second analytes or an identical second analyte at different concentrations. In some embodiments, one, at least one, or each, of the second plurality of droplets comprises an identical second analyte, and two droplets of the first plurality of droplets comprise different first analytes or an identical first analyte at different concentrations. In some embodiments, the first analyte is a drug and the second analyte is an enzyme capable of metabolizing the drug to a product (or a metabolite), or the first analyte is an enzyme substrate and the second substrate is an enzyme capable of converting the enzyme substrate to a product. In some embodiments, the second analyte is a drug and the first analyte is an enzyme capable of metabolizing the drug to a product (or a metabolite), or the second analyte is an enzyme substrate and the first substrate is an enzyme capable of converting the enzyme substrate to a product.

Disclosed herein include embodiments of a device for sample deposition on a mass spectrometry surface. In some embodiments, the device comprises an array of wells. The wells can be sized and/or shaped to capture one or more (such as 1, 2, 3, 4, 5, 6, 7, 8, 9, 10, or more) of a first plurality of droplets each comprising one or more first analytes. The device can comprise: a mass spectrometry (MS) chip. The device can comprise: a reversible sealing mechanism comprising a top clamp and a bottom clamp. The top clamp can be located above, or in contact with, one of the array of wells and the mass spectrometry chip. The bottom clamp can be located below, or in contact with, the other of the array of wells and the mass spectrometry chip, the reversible sealing mechanism can be configured to adjust a distance (or a space) between a well-opening surface of the array of the wells and the mass spectrometry surface of the MS chip to be between zero to about 50 mm.

Disclosed herein include embodiments of a microfluidic device reversibly sealed to a laser desorption/ionization mass spectrometry (MS) surface. The microfluidic device can be a polymeric microfluidic device. The microfluidic device can be reversibly sealed to the laser desorption/ionization mass spectrometry surface with a reversible sealing mechanism comprising a top clamp and a bottom clamp. The top clamp can be located above, or in contact with, one of an array of wells and a MS chip comprising the laser desorption/ionization MS surface. The bottom clamp can be located below, or in contact with, the other of the array of wells and the MS chip. The reversible sealing mechanism can be configured to adjust a distance (or a space) between a well-opening surface of the array of the wells and the mass spectrometry surface of the MS chip to be between zero to about 50 mm. In some embodiments, a MS chip comprises the laser desorption/ionization MS surface. In some embodiments, the wells are sized and/or shaped to capture one or more (such as 1, 2, 3, 4, 5, 6, 7, 8, 9, 10, or more) of a first plurality of droplets each comprising one or more first analytes.

In some embodiments, the array of wells is positioned with the well-opening surface facing down (or up), and the mass spectrometry chip is positioned with mass spectrometry surface facing up (or down).

In some embodiments, the top clamp is a clamping plate located above a side of the array of wells opposite of the well-opening surface of the array of wells, and the bottom clamp is a clamping plate located below a side of the mass spectrometry chip opposite of the mass spectrometry surface.

In some embodiments, the device comprises a droplet loading mechanism. The droplet loading mechanism can comprise an inlet for loading the first plurality of droplets in a solvent-in-oil emulsion.

In some embodiments, the mass spectrometry chip is a mass spectrometry chip for laser desorption/ionization MS. The laser desorption/ionization MS can be nanostructure-initiator mass spectrometry (NIMS), desorption/ionization on silicon (DIOS) MS, nanowire-assisted laser desorption/ionization (NALDI) MS, insulator nanostructure desorption ionization (INDI) MS, nanopost array laser desorption ionization (NAPA) MS, matrix-assisted laser desorption/ionization (MALDI) MS, surface-assisted laser desorption/ionization (SALDI) MS, surface-enhanced laser desorption/ionization (SELDI) MS, or a combination thereof.

In some embodiments, the space between the mass spectrometry surface and the well-opening surface of the array of the wells is adjustable between zero to about 20 mm, between zero to about 10 mm, between zero to about 5 mm, or between zero to about 1 mm.

In some embodiments, the wells of the array are each sized and/or shaped to capture no more than one of the first plurality of droplets (such as 1, 2, 3, 4, 5, 6, 7, 8, 9, 10, or more droplets). The wells of the array can be each sized and/or shaped to capture two, three, four, five, or more of the first plurality of droplets. The wells of the array each can be sized and/or shaped to capture (i) at most one of the droplets from the first plurality of droplets, and (ii) at most one of the droplets from a second plurality of droplets when the droplet from the first plurality of droplets is captured in the well of the array.

A dimension of each of more than 50%, more than 75%, or more than 95% of the wells in the array of wells can be about 20 µm to about 410 µm, 30 µm to about 210 µm, or about 80 µm to about 160 µm. A dimension of each of more than 50%, more than 75%, or more than 95% of the wells in the array of wells can be about 150 µm to about 310 µm. The dimension can be a width, a height, a depth, or a combination thereof, of the well.

In some embodiments, the array of wells comprises a material selected from the group consisting of cyclic olefin copolymer (COC), polycarbonate (PC), poly(dimethylsiloxane) (PDMS), poly(methylacrylate) (PMMA), polystyrene (PS), polypropylene (PP), polyethylene terephthalate (PET), an elastomer, a glass, a synthesized hydrogel, and a combination thereof. The side of the array of wells opposite of the well-opening surface of the array of wells can be in contact with an additional layer, optionally the additional layer comprises a glass layer.

Disclosed herein include embodiments of a device for screening for an enzyme substrate, for screening for an enzyme capable of catalyzing a substrate to a product, for screening analytes (such as enzymes and substrates), or for sample deposition on a mass spectrometry surface. In some embodiments, the system comprises an imaging device for optically identifying first analytes deposited onto the mass spectrometry surface.

Details of one or more implementations of the subject matter described in this specification are set forth in the accompanying drawings and the description below. Other features, aspects, and advantages will become apparent from the description, the drawings, and the claims. Neither this summary nor the following detailed description purports to define or limit the scope of the inventive subject matter.

BRIEF DESCRIPTION OF THE DRAWINGS

FIG. 1A shows a non-limiting exemplary schematic illustration of a droplet array generation apparatus. FIG. 1B shows a perspective view and a top view of a non-limiting exemplary schematic illustration of a loading chip (e.g., a PDMS loading chip) sealed against a MS surface (e.g., a NIMS surface). FIG. 1C shows a cross section view of a non-limiting exemplary schematic illustration of droplet loading. FIG. 1D shows a non-limiting exemplary photograph of a loading chip (left), a perspective view of a non-limiting exemplary schematic illustration of the loading chip (middle), and a cross section view a non-limiting exemplary schematic illustration of the loading chip in contact with the MS surface (right).

FIG. 3A shows an illustration of the laser irradiation on NIMS surface resulting in desorption of sample. FIG. 3B shows a photograph of NIMS surface (5 cm×5 cm) with a zoomed-in scanning electron microscope (SEM) image of nanostructured surface.

FIGS. 4A-4J show micrographs and schematic illustrations of droplet loading chips with two different designs (120 µm deep); 'Single' (120 µm diameter, FIGS. 4A and 4C) or 'Double' (120 µm×240 µm in dimensions, FIGS. 4B, 4D, and 4F) geometries, (FIGS. 4G-4H) Bright-field images and (FIGS. 4I-4J) On-chip fluorescence imaging of trapped droplets. FIG. 4E shows a schematic illustration of a 'Double' well geometry.

FIG. 6A: Verapamil (green), and FIG. 6B: G2-Ftag (red). Successful sample deposition with no leakage or cross-contamination. MS imaging conditions: Raster width 50 µm on AB Sciex5800 MALDI TOF/TOF.

FIG. 7A shows non-limiting exemplary ion intensity maps of G2-Ftag, G1-Ftag, and Ftag. Each spot in the ion intensity map shows the quantity of G2-Ftag, G1-Ftag, or Ftag in a well as detected by MS. FIG. 7C shows a non-limiting exemplary MS spectrum showing all three components (G2-Ftag, G1-Ftag, and Ftag) in a well.

FIGS. 8A-8C show deposition and detection of mass spectrometry barcodes in droplets which can be used as sample identifiers. Each droplet contained one of five lanthanide barcodes. Each of the five lanthanide barcodes comprised a lanthanide chelator in complex with a different lanthanide metal. The droplet loading chip used could hold two droplets per well, and each well of a loading chip can be used to load up to two lanthanide barcodes onto the MS surface. FIG. 8B shows ion intensity maps of each lanthanide barcode (2500 um×2500 um images 40 um step size raster). FIG. 8C shows merged ion intensity maps of three lanthanide barcodes, illustrating that each well of the loading chip loaded up to two lanthanide barcodes onto the MS surface.

DETAILED DESCRIPTION

Figure 1A:
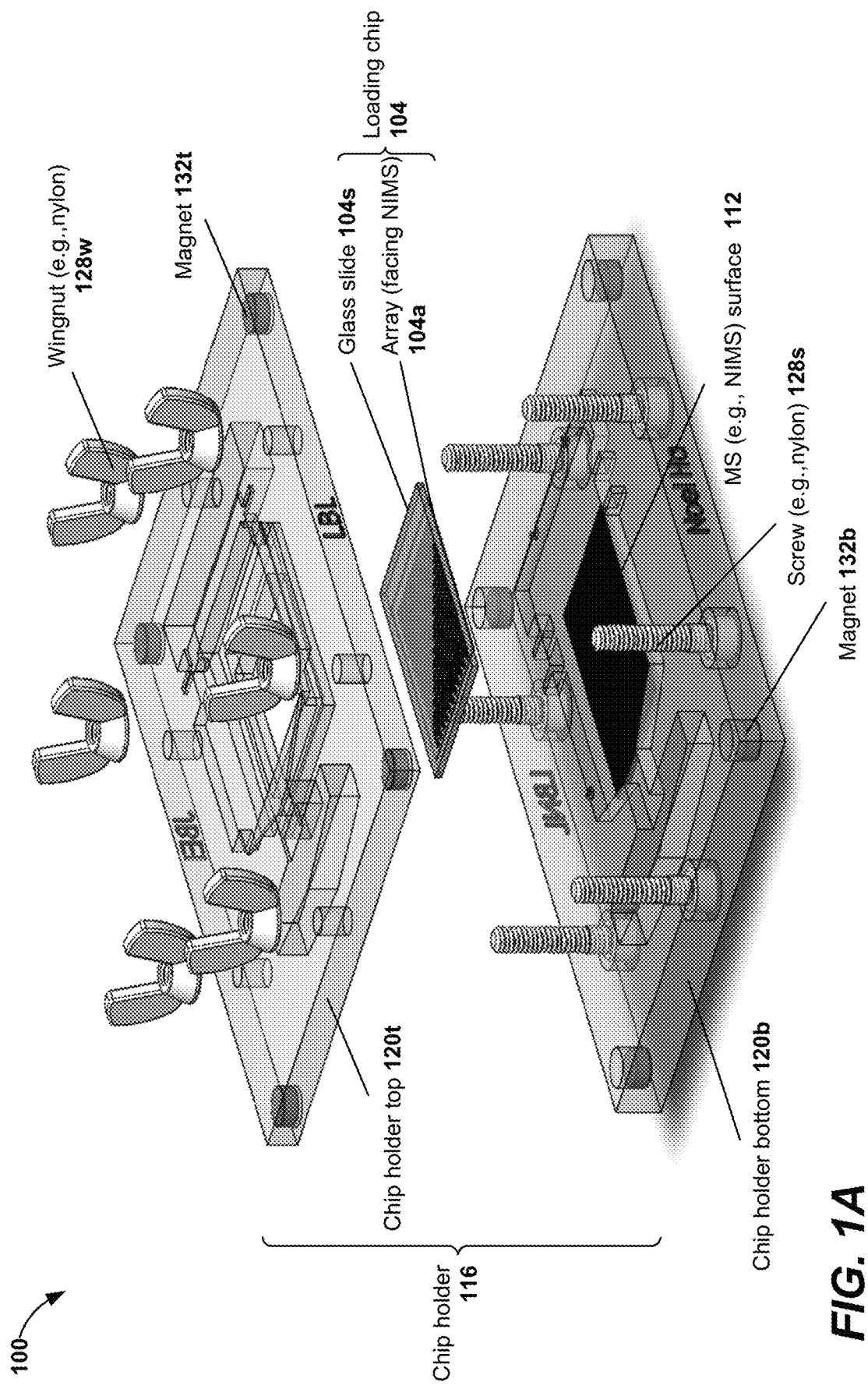
FIGS. 1A-1D show non-limiting exemplary schematic illustrations of a droplet array generation apparatus with a MS surface (e.g., a nanostructured-initiator MS (NIMS) surface). The PDMS chip can be initially positioned above NIMS with a 1 mm gap during droplet loading step (FIG. 1C), then sealed against NIMS surface upon completion.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein and made part of the disclosure herein.

All patents, published patent applications, other publications, and sequences from GenBank, and other databases referred to herein are incorporated by reference in their entirety with respect to the related technology.

Definitions

Unless defined otherwise, technical and scientific terms used herein have the same meaning as commonly understood by one of ordinary skill in the art to which the present disclosure belongs. See, e.g., Singleton et al., Dictionary of Microbiology and Molecular Biology 2nd ed., J. Wiley & Sons (New York, N.Y. 1994); Sambrook et al., Molecular Cloning, A Laboratory Manual, Cold Spring Harbor Press (Cold Spring Harbor, N.Y. 1989). For purposes of the present disclosure, the following terms are defined below.

Overview

Disclosed herein include embodiments of a droplet microfluidic platform, system, device and approach that can enable rapid sample preparation at a massive scale directly above a mass spectrometry surface (e.g., a matrix-free mass spectrometry surface) for high-throughput combinatorial screening of enzymatic activity to expand the understanding of important enzyme classes. The microfluidic platform can have broad applications, ranging from discovery of new enzymes and complex multi-step metabolic pathways to support synthetic biology and bioenergy production as well as drug development.

In some embodiments, the approach includes the coupling of a matrix-free surface-based mass spectrometry imaging, nanostructure-initiator mass spectrometry (NIMS), with droplet microfluidics for screening enzyme activities at a massive scale. The system can enable rapid droplet array generations (<10 min), on-chip enzymatic reaction and sample deposition, and most importantly MS imaging (2D surface scanning of ion intensity). Through picoliter droplet array construction on the NIMS surface, up to 100,000 metabolite analyses can be screened on a single microfluidic chip.

In some embodiments, a PDMS microfluidic droplet loading chip with an array of wells (100-150 μm depth and diameter) is fabricated for entrapment of picoliter droplets directly above the NIMS surface. The NIMS surface is prepared as previously described (Northen et al. 2007 Nature, 449, 1033-1036, the content of which is incorporated herein by reference in its entirety). Droplets (100-150 μm diameter) can be either manually or automatically loaded onto chips, then single or multiple droplets can be randomly trapped and paired into the wells depending on the well geometry, up to 100,000 droplets in a single-droplet well design. The fast droplet entrapment can occur by the oil flow and droplet buoyancy. After the completion of droplet loading, the loading chip can be sealed against the NIMS surface to confine droplets, followed by droplet merging and enzymatic reaction. Volatile carrier oil can evaporate through the gas-permeable PDMS, resulting in sample deposition via direct contact between droplet and NIMS surface. After evaporation (e.g., complete evaporation) of oil and solvent, the NIMS surface can be separated from the droplet loading chip for mass spectrometry imaging (MSI) on a MALDI MS system. On-chip droplet fluorescence imaging can be optionally performed on a plate imager (e.g., an automated plate imager) for droplet identification and colorimetric assay. Additionally, the droplet loading chip design can be flexible to accommodate more droplets per site, suitable for an investigation of complex combinatorial and synergistic effects.

Sample Deposition Devices

Disclosed herein include embodiments of a device 100 for sample deposition on a mass spectrometry surface. FIGS. 1A-1D show non-limiting exemplary schematic illustrations of the device 100 for sample deposition. In some embodiments, the device 100 comprises an array 104a of wells 104w (e.g., wells, nanowells, or picowells) or a loading chip 104 comprising an array 104a of wells 104w. The loading chip 104 can comprise two layers, the array 104a layer and a second or additional layer 104s (e.g., a glass slide). For example, the loading chip 104 can be a PDMS-on-glass chip with the PDMS layer comprising the array 104a and a glass layer as the second layer 104s. A voltage (e.g., an AC voltage) can be applied to the loading chip (e.g., to the array 104a and/or to the second layer 104s) for merging droplets in wells 104w of the array 104a. The wells 104w can be sized and/or shaped to capture one or more 108l of a first plurality of droplets 108 each comprising one or more first analytes. The device 100 can comprise: a mass spectrometry (MS) chip 112. The device 100 can comprise: a reversible sealing mechanism 116 (e.g., a chip holder) comprising a top clamp (or chip holder top) 120t and a bottom clamp (or chip holder bottom) 120b. The top clamp 120t can be located above, or in contact with, the array 104a of wells 104w, and the bottom clamp 120b can be located below, or in contact with, the mass spectrometry chip 112 as illustrated in FIGS. 1A and 1C. In some embodiments, the top clamp 120t can be located above, or in contact with, the mass spectrometry chip 112, and the bottom clamp 120b can be located below, or in contact with, the array 104a of wells 104w.

Referring to FIGS. 1A-1D, the reversible sealing mechanism 116 can be configured to adjust a distance (or a space) or a distance 124 between a well-opening surface 104o of the array 104a of the wells 104w and a mass spectrometry surface 112s of the MS chip 112 to be between, for example, zero to about 50 mm. In the embodiments illustrated in FIGS. 1A-1C, the reversible sealing mechanism 116 can include a tightening mechanism, such as screws 128s and wingnuts 128w (e.g., nylon screws 128s and wingnuts 128w), for adjusting the (maximum) space between the top clamp 120t and the bottom clamp 120b. The tightening mechanism can be used to adjust the (maximum) space the well-opening surface 104o of the array and the mass spectrometry surface 112s. The top clamp 120t and the bottom clamp 120b can include magnets 132t, 132b for maintaining the space between the top clamp 120t and the bottom clamp 120b.

In some embodiments, the space 124 between the mass spectrometry surface 112s and the well-opening surface 104o of the array 104a of the wells 104w is adjustable between zero to about 20 mm, between zero to about 10 mm, between zero to about 5 mm, or between zero to about 1 mm. In some embodiments, the space 124 between the well-opening surface 104o of the array and the mass spectrometry surface 112s can be, be about, be at least, or be at most, 0 mm, 0.01 mm, 0.02 mm, 0.03 mm, 0.04 mm, 0.05 mm, 0.06 mm, 0.07 mm, 0.08 mm, 0.09 mm, 0.1 mm, 0.2 mm, 0.3 mm, 0.4 mm, 0.5 mm, 0.6 mm, 0.7 mm, 0.8 mm, 0.9 mm, 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, 25 mm, 26 mm, 27 mm, 28 mm, 29 mm, 30 mm, 31 mm, 32 mm, 33 mm, 34 mm, 35 mm, 36 mm, 37 mm, 38 mm, 39 mm, 40 mm, 41 mm, 42 mm, 43 mm, 44 mm, 45 mm, 46 mm, 47 mm, 48 mm, 49 mm, 50 mm, or a number or a range between any two of these values.

Disclosed herein include embodiments of a microfluidic device 100 reversibly sealed to a laser desorption/ionization mass spectrometry (MS) surface 112s. The microfluidic device 100 can be a polymeric microfluidic device. The microfluidic device 100 can be reversibly sealed to the laser desorption/ionization mass spectrometry surface with a reversible sealing mechanism 116 comprising a top clamp 120t and a bottom clamp 120b. The top clamp 120t can be located above, or in contact with, one of an array 104a of wells 104w and a MS chip 112 comprising the laser desorption/ionization MS surface 112s. The bottom clamp 120b can be located below, or in contact with, the other of the array 104a of wells 104w and the MS chip 112s. The reversible sealing mechanism 116 can be configured to adjust a distance (or a space) 124 between a well-opening surface 104o of the array 104a of the wells 104w and the mass spectrometry surface 112s of the MS chip 112 to be between zero to about 50 mm. In some embodiments, a MS chip 112 comprises the laser desorption/ionization MS surface. In some embodiments, the wells 104w are sized and/or shaped to capture one or more 108l of a first plurality of droplets 108 each comprising one or more first analytes.

In some embodiments, the array 104a of wells 104w is positioned with the well-opening surface 104o facing down, and the mass spectrometry chip is positioned with mass spectrometry surface 112s facing up as illustrated in FIGS. 1A and 1C. In some embodiments, the array 104a of wells 104w is positioned with the well-opening surface 104o facing up, and the mass spectrometry chip is positioned with mass spectrometry surface 112s facing down.

In some embodiments, the top clamp 120t is a clamping plate located above a side 104t of the array 104a of wells 104w opposite of the well-opening surface 104o of the array 104a of wells 104w, and the bottom clamp is a clamping plate located below a side 112b of the mass spectrometry chip 112 opposite of the mass spectrometry surface 112 as illustrated in FIGS. 1A and 1C. In some embodiments, the top clamp 120t is a clamping plate located above a side 112b of the mass spectrometry chip 112 opposite of the mass spectrometry surface 112, and the bottom clamp is a clamping plate located below a side 104t of the array 104a of wells 104w opposite of the well-opening surface 104o of the array 104a of wells 104w. The top clamp 120t and/or the bottom clamps 120b can comprise a loading chip mounting slot sized to hold the loading chip 104.

In some embodiments, the device 100 comprises a window 136w in the top clamp 120t for applying a voltage (e.g., an alternative current (AC) voltage) to the loading chip 104 (e.g., the array 104a or the second layer 104s, such as a glass layer of the loading chip 104), not the MS chip 112, for merging droplets in wells. In some embodiments, the device 100 comprises a droplet loading mechanism. The droplet loading mechanism can comprise an inlet 136i and an outlet 136o for loading the first plurality of droplets. The droplets from the first plurality of droplets can be, for example, solvent-in-oil emulsions or oil-in-solvent emulsions. The droplets from the first plurality of droplets can be loaded via a carrier fluid, such as an oil.

Array and Wells of Array

Figure 4I:
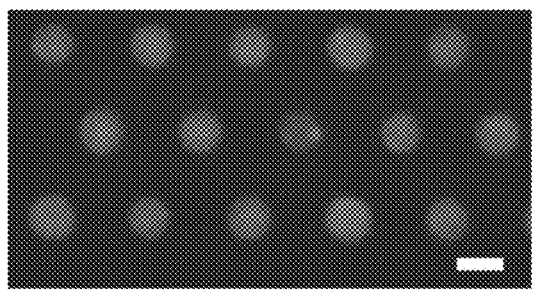
Figure 4J:
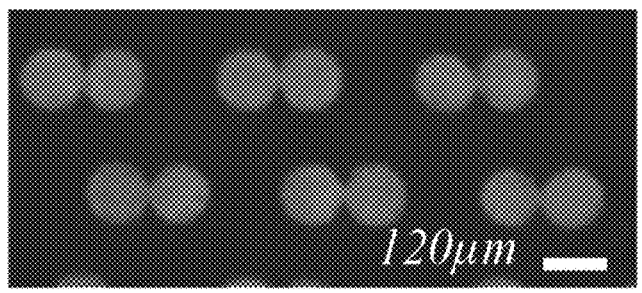
Figure 4K:
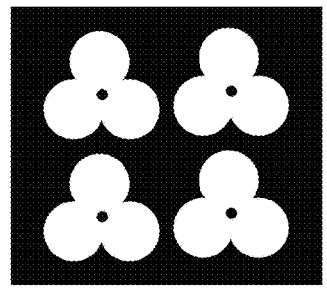
FIGS. 4K-4L show schematic illustrations of 'Triple' well geometries.
Figure 4L:
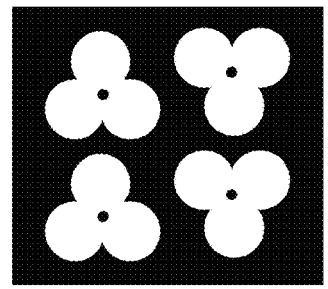
Figure 4M:
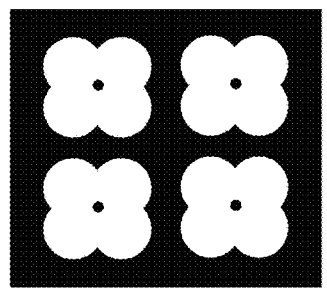
FIG. 4M show a schematic illustration of a 'Quadruple' geometry.

In some embodiments, the wells of the array are each sized and/or shaped to capture no more than one (see FIGS. 4A, 4C, 4G, and 4I for examples) of the first plurality of droplets. The wells of the array can be each sized and/or shaped to capture two (see FIGS. 4B, 4D, 4E, 4F, 4H, and 4J for examples), three, four, five, or more of the first plurality of droplets. In some embodiments, each well can be sized and/or shaped to capture, to capture about, or to capture at most, 1, 2, 3, 4, 5, 6, 7, 8, 9, 10, or a number or a range between any two of these values, droplets. FIG. 4C shows a schematic illustration of a well geometry for capturing one droplet. FIGS. 4D-4E show schematic illustrations of well geometries for capturing two droplets. FIGS. 4K-4L show schematic illustrations of well geometries for capturing three droplets. FIG. 4M show a schematic illustration of a well geometry for capturing three droplets. The wells of the array each can be sized and/or shaped to capture (i) at most one of the droplets from the first plurality of droplets, and (ii) at most one of the droplets from a second plurality of droplets when the droplet from the first plurality of droplets is captured in the well of the array. For example, as illustrated in FIG. 4E, a well can include a volume (or a space) with a larger dimension for capturing a larger droplet and a volume (or a space) with a smaller dimension for capturing a smaller droplet. By loading the larger droplet before loading the smaller droplet, the well can include one larger droplet and one smaller droplet. As another example, a well can include a volume (or a space) with a larger dimension for capturing a larger droplet, a volume (or a space) with a medium dimension for capturing a medium size droplet, and a volume (or a space) with a smaller dimension for capturing a smaller droplet. By loading the larger droplet before loading the medium size droplet and loading the medium size droplet before loading the smaller droplet, the well can include one larger droplet, one medium size droplet, and one smaller droplet. The number of spaces per well can be different in different embodiments, such as 1, 2, 3, 4, 5, 6, 7, 8, 9, 10, or a number or a range between any two of these values.

A dimension of each of more than 50%, more than 75%, or more than 95% of the wells in the array of wells can be about 20 µm to about 410 µm, 30 µm to about 210 µm, or about 80 µm to about 160 µm. A dimension of each of more than 50%, more than 75%, or more than 95% of the wells in the array of wells can be about 150 µm to about 310 µm. The dimension can be a width, a height, a depth, a diameter, or a combination thereof, of the well. A dimension (e.g., a width, a height, a depth, or a diameter) of each of a percentage (e.g., 75%) of the wells in the array of wells can be a particular size (e.g., 160 µm). The percentage of the wells in the array with a particular size can be, be about, be at least, or be at most, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, or a number or a range between any two of these values. The size of a dimension of a well can be, be about, be at least, or be at most, 1 µm, 2 µm, 3 µm, 4 µm, 5 µm, 6 µm, 7 µm, 8 µm, 9 µm, 10 µm, 10 µm, 20 µm, 30 µm, 40 µm, 50 µm, 60 µm, 70 µm, 80 µm, 90 µm, 100 µm, 110 µm, 120 µm, 130 µm, 140 µm, 150 µm, 160 µm, 170 µm, 180 µm, 190 µm, 200 µm, 210 µm, 220 µm, 230 µm, 240 µm, 250 µm, 260 µm, 270 µm, 280 µm, 290 µm, 300 µm, 310 µm, 320 µm, 330 µm, 340 µm, 350 µm, 360 µm, 370 µm, 380 µm, 390 µm, 400 µm, 410 µm, 420 µm, 430 µm, 440 µm, 450 µm, 460 µm, 470 µm, 480 µm, 490 µm, 500 µm, 510 µm, 520 µm, 530 µm, 540 µm, 550 µm, 560 µm, 570 µm, 580 µm, 590 µm, 600 µm, 610 µm, 620

µm, 630 µm, 640 µm, 650 µm, 660 µm, 670 µm, 680 µm, 690 µm, 700 µm, 710 µm, 720 µm, 730 µm, 740 µm, 750 µm, 760 µm, 770 µm, 780 µm, 790 µm, 800 µm, 810 µm, 820 µm, 830 µm, 840 µm, 850 µm, 860 µm, 870 µm, 880 µm, 890 µm, 900 µm, 910 µm, 920 µm, 930 µm, 940 µm, 950 µm, 960 µm, 970 µm, 980 µm, 990 µm, 1 mm, 2 mm, 3 mm, 4 mm, 5 mm, 6 mm, 7 mm, 8 mm, 9 mm, 10 mm, or a number or a range between any two of these values.

The volume of a well can be different in different implementations. In some embodiments, the well can be, be about, be at least, or be at most, 1 pl, 2 pl, 3 pl, 4 pl, 5 pl, 6 pl, 7 pl, 8 pl, 9 pl, 10 pl, 20 pl, 30 pl, 40 pl, 50 pl, 60 pl, 70 pl, 80 pl, 90 pl, 100 pl, 110 pl, 120 pl, 130 pl, 140 pl, 150 pl, 160 pl, 170 pl, 180 pl, 190 pl, 200 pl, 210 pl, 220 pl, 230 pl, 240 pl, 250 pl, 260 pl, 270 pl, 280 pl, 290 pl, 300 pl, 310 pl, 320 pl, 330 pl, 340 pl, 350 pl, 360 pl, 370 pl, 380 pl, 390 pl, 400 pl, 410 pl, 420 pl, 430 pl, 440 pl, 450 pl, 460 pl, 470 pl, 480 pl, 490 pl, 500 pl, 510 pl, 520 pl, 530 pl, 540 pl, 550 pl, 560 pl, 570 pl, 580 pl, 590 pl, 600 pl, 610 pl, 620 pl, 630 pl, 640 pl, 650 pl, 660 pl, 670 pl, 680 pl, 690 pl, 700 pl, 710 pl, 720 pl, 730 pl, 740 pl, 750 pl, 760 pl, 770 pl, 780 pl, 790 pl, 800 pl, 810 pl, 820 pl, 830 pl, 840 pl, 850 pl, 860 pl, 870 pl, 880 pl, 890 pl, 900 pl, 910 pl, 920 pl, 930 pl, 940 pl, 950 pl, 960 pl, 970 pl, 980 pl, 990 pl, 1000 pl, 2 nl, 3 nl, 4 nl, 5 nl, 6 nl, 7 nl, 8 nl, 9 nl, 10 nl, 20 nl, 30 nl, 40 nl, 50 nl, 60 nl, 70 nl, 80 nl, 90 nl, 100 nl, 110 nl, 120 nl, 130 nl, 140 nl, 150 nl, 160 nl, 170 nl, 180 nl, 190 nl, 200 nl, 210 nl, 220 nl, 230 nl, 240 nl, 250 nl, 260 nl, 270 nl, 280 nl, 290 nl, 300 nl, 310 nl, 320 nl, 330 nl, 340 nl, 350 nl, 360 nl, 370 nl, 380 nl, 390 nl, 400 nl, 410 nl, 420 nl, 430 nl, 440 nl, 450 nl, 460 nl, 470 nl, 480 nl, 490 nl, 500 nl, 510 nl, 520 nl, 530 nl, 540 nl, 550 nl, 560 nl, 570 nl, 580 nl, 590 nl, 600 nl, 610 nl, 620 nl, 630 nl, 640 nl, 650 nl, 660 nl, 670 nl, 680 nl, 690 nl, 700 nl, 710 nl, 720 nl, 730 nl, 740 nl, 750 nl, 760 nl, 770 nl, 780 nl, 790 nl, 800 nl, 810 nl, 820 nl, 830 nl, 840 nl, 850 nl, 860 nl, 870 nl, 880 nl, 890 nl, 900 nl, 910 nl, 920 nl, 930 nl, 940 nl, 950 nl, 960 nl, 970 nl, 980 nl, 990 nl, 1000 nl, or a number or a range between any two of these values.

The number of wells 104w in the array 104a can be different in different implementations. In some embodiments, the number of wells 104w in the array 104a can be, be about, be at least, or be at most, 100, 200, 300, 400, 500, 600, 700, 800, 900, 1000, 2000, 3000, 4000, 5000, 6000, 7000, 8000, 9000, 10000, 11000, 12000, 13000, 14000, 15000, 16000, 17000, 18000, 19000, 20000, 21000, 22000, 23000, 24000, 25000, 26000, 27000, 28000, 29000, 30000, 31000, 32000, 33000, 34000, 35000, 36000, 37000, 38000, 39000, 40000, 41000, 42000, 43000, 44000, 45000, 46000, 47000, 48000, 49000, 50000, 51000, 52000, 53000, 54000, 55000, 56000, 57000, 58000, 59000, 60000, 61000, 62000, 63000, 64000, 65000, 66000, 67000, 68000, 69000, 70000, 71000, 72000, 73000, 74000, 75000, 76000, 77000, 78000, 79000, 80000, 81000, 82000, 83000, 84000, 85000, 86000, 87000, 88000, 89000, 90000, 91000, 92000, 93000, 94000, 95000, 96000, 97000, 98000, 99000, 100000, 200000, 300000, 400000, 500000, 600000, 700000, 800000, 900000, 1000000, or a number or a range between any two of these values.

Array Material

In some embodiments, the array of wells comprises a material selected from the group consisting of cyclic olefin copolymer (COC), polycarbonate (PC), poly(dimethylsiloxane) (PDMS), poly(methylacrylate) (PMMA), polystyrene (PS), polypropylene (PP), polyethylene terephthalate (PET), an elastomer, a glass, a synthesized hydrogel, and a combination thereof. An elastomer (elastic polymer) can comprise a rubber, an unsaturated rubber, a natural polyisoprene rubber, a synthetic polyisoprene rubber, a polybutadiene rubber, a chloroprene rubber, a butyl rubber, a styrene-butadiene rubber, a nitrile rubber, a saturated rubber, an ethylene propylene rubber, an epichlorohydrin rubber, a polyacrylic rubber, a silicone rubber, a fluorosilicone rubber, a fluoroelastomer a perfluoroelastomer, a polyether block amides rubber, a chlorosulfonated polyethylene rubber, an ethylene-vinyl acetate rubber, a thermoplastic elastomer, a polysulfide rubber, or a combination thereof.

The permeability of the material of the array can be different in different implementations. In some embodiments, the material of the array has a permeability with respect to the carrier fluid, the solvent of the solvent-in-oil emulsion or oil-in-solvent emulsion, and/or the oil in solvent-in-oil emulsion or the oil-in-solvent emulsion of 0.001 m$^2$, 0.002 m$^2$, 0.003 m$^2$, 0.004 m$^2$, 0.005 m$^2$, 0.006 m$^2$, 0.007 m$^2$, 0.008 m$^2$, 0.009 m$^2$, 0.01 m$^2$, 0.02 m$^2$, 0.03 m$^2$, 0.04 m$^2$, 0.05 m$^2$, 0.06 m$^2$, 0.07 m$^2$, 0.08 m$^2$, 0.09 m$^2$, 0.1 m$^2$, 0.2 m$^2$, 0.3 m$^2$, 0.4 m$^2$, 0.5 m$^2$, 0.6 m$^2$, 0.7 m$^2$, 0.8 m$^2$, 0.9 m$^2$, 1 m$^2$, or a number or a range between any two of these values. In some embodiments, the material of the array has a permeability with respect to the carrier fluid, the solvent of the solvent-in-oil emulsion, and/or the oil in solvent-in-oil emulsion of 1, 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, or a number or a range between any two of these values, darcy units.

Array Dimension

The size of the array 104a layer (e.g., a PDMS array layer) can be different in different embodiments. In some embodiments, the width of the array layer 104a can be, can be about, can be at most, or can be at least, 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, 25 mm, 26 mm, 27 mm, 28 mm, 29 mm, 30 mm, 31 mm, 32 mm, 33 mm, 34 mm, 35 mm, 36 mm, 37 mm, 38 mm, 39 mm, 40 mm, 41 mm, 42 mm, 43 mm, 44 mm, 45 mm, 46 mm, 47 mm, 48 mm, 49 mm, 50 mm, 51 mm, 52 mm, 53 mm, 54 mm, 55 mm, 56 mm, 57 mm, 58 mm, 59 mm, 60 mm, 61 mm, 62 mm, 63 mm, 64 mm, 65 mm, 66 mm, 67 mm, 68 mm, 69 mm, 70 mm, 71 mm, 72 mm, 73 mm, 74 mm, 75 mm, 76 mm, 77 mm, 78 mm, 79 mm, 80 mm, 81 mm, 82 mm, 83 mm, 84 mm, 85 mm, 86 mm, 87 mm, 88 mm, 89 mm, 90 mm, 91 mm, 92 mm, 93 mm, 94 mm, 95 mm, 96 mm, 97 mm, 98 mm, 99 mm, 100 mm, or a number or a range between any two of these values.

In some embodiments, the length of the array 104a layer can be, can be about, can be at most, or can be at least, 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, 25 mm, 26 mm, 27 mm, 28 mm, 29 mm, 30 mm, 31 mm, 32 mm, 33 mm, 34 mm, 35 mm, 36 mm, 37 mm, 38 mm, 39 mm, 40 mm, 41 mm, 42 mm, 43 mm, 44 mm, 45 mm, 46 mm, 47 mm, 48 mm, 49 mm, 50 mm, 51 mm, 52 mm, 53 mm, 54 mm, 55 mm, 56 mm, 57 mm, 58 mm, 59 mm, 60 mm, 61 mm, 62 mm, 63 mm, 64 mm, 65 mm, 66 mm, 67 mm, 68 mm, 69 mm, 70 mm, 71 mm, 72 mm, 73 mm, 74 mm, 75 mm, 76 mm, 77 mm, 78 mm, 79 mm, 80 mm, 81 mm, 82 mm, 83 mm, 84 mm, 85 mm, 86 mm, 87 mm, 88 mm, 89 mm, 90 mm, 91 mm, 92 mm, 93 mm, 94 mm, 95 mm, 96 mm, 97 mm, 98 mm, 99 mm, 100 mm, or a number or a range between any two of these values.

In some embodiments, the height or the thickness of the array 104a layer can be, can be about, can be at most, or can be at least, 10 µm, 20 µm, 30 µm, 40 µm, 50 µm, 60 µm, 70 µm, 80 µm, 90 µm, 100 µm, 110 µm, 120 µm, 130 µm, 140 µm, 150 µm, 160 µm, 170 µm, 180 µm, 190 µm, 200 µm, 210 µm, 220 µm, 230 µm, 240 µm, 250 µm, 260 µm, 270 µm, 280 µm, 290 µm, 300 µm, 310 µm, 320 µm, 330 µm, 340 µm, 350 µm, 360 µm, 370 µm, 380 µm, 390 µm, 400 µm, 410 µm, 420 µm, 430 µm, 440 µm, 450 µm, 460 µm, 470 µm, 480 µm, 490 µm, 500 µm, 510 µm, 520 µm, 530 µm, 540 µm, 550 µm, 560 µm, 570 µm, 580 µm, 590 µm, 600 µm, 610 µm, 620 µm, 630 µm, 640 µm, 650 µm, 660 µm, 670 µm, 680 µm, 690 µm, 700 µm, 710 µm, 720 µm, 730 µm, 740 µm, 750 µm, 760 µm, 770 µm, 780 µm, 790 µm, 800 µm, 810 µm, 820 µm, 830 µm, 840 µm, 850 µm, 860 µm, 870 µm, 880 µm, 890 µm, 900 µm, 910 µm, 920 µm, 930 µm, 940 µm, 950 µm, 960 µm, 970 µm, 980 µm, 990 µm, 1 mm, 2 mm, 3 mm, 4 mm, 5 mm, 6 mm, 7 mm, 8 mm, 9 mm, 10 mm, or a number or a range between any two of these values.

Second Layer Material

In some embodiments, the second or additional layer 104s can be a glass layer. In some embodiments, the glass layer comprises a glass slide. The material of the second or additional layer 104 can be different in different embodiments. In some embodiments, the material of the glass of the second layer 104s (or any glass of the present disclosure) comprises an oxide, silicon dioxide (e.g., fused quartz), sodium carbonate, boron trioxide (e.g., borosilicate glass), lead(II) oxide, alumina (e.g., aluminosilicate glass), barium, lanthanum oxide, iron oxide, cerium(IV) oxide, a halide (e.g., fluoride), a glass-ceramic material, a fiberglass material, or a combination thereof. In some embodiments, the glass of the second layer 104s (or any glass of the present disclosure) is a non-silica-based glass. For example, the material of the glass can comprise inorganic and organic materials, including metals, aluminates, phosphates, borates, chalcogenides, fluorides, germanates (glass based on GeO), tellurites (glass based on $TeO_2$), antimonates (glass based on $Sb_2O_3$), arsenates (glass based on $As_2O_3$), titanates (glass based on $TiO_2$), tantalates (glass based on $Ta_2O_5$), nitrates, carbonates, plastics, acrylic, or a combination thereof. In some embodiments, the glass of the second layer 104s (or any glass of the present disclosure) is a polymer glass, such as acrylic glass, polycarbonate glass, and polyethylene terephthalate glass.

Second Layer Dimension

The size of the second layer 104s (e.g., a glass layer) can be different in different embodiments. For example, the glass slide can have a size of 25.4 mm (width)×40 mm (length)×1 mm (height or thickness). In some embodiments, the width of the second layer 104s can be, can be about, can be at most, or can be at least, 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, 25 mm, 26 mm, 27 mm, 28 mm, 29 mm, 30 mm, 31 mm, 32 mm, 33 mm, 34 mm, 35 mm, 36 mm, 37 mm, 38 mm, 39 mm, 40 mm, 41 mm, 42 mm, 43 mm, 44 mm, 45 mm, 46 mm, 47 mm, 48 mm, 49 mm, 50 mm, 51 mm, 52 mm, 53 mm, 54 mm, 55 mm, 56 mm, 57 mm, 58 mm, 59 mm, 60 mm, 61 mm, 62 mm, 63 mm, 64 mm, 65 mm, 66 mm, 67 mm, 68 mm, 69 mm, 70 mm, 71 mm, 72 mm, 73 mm, 74 mm, 75 mm, 76 mm, 77 mm, 78 mm, 79 mm, 80 mm, 81 mm, 82 mm, 83 mm, 84 mm, 85 mm, 86 mm, 87 mm, 88 mm, 89 mm, 90 mm, 91 mm, 92 mm, 93 mm, 94 mm, 95 mm, 96 mm, 97 mm, 98 mm, 99 mm, 100 mm, or a number or a range between any two of these values.

In some embodiments, the length of the second layer 104s can be, can be about, can be at most, or can be at least, 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, 25 mm, 26 mm, 27 mm, 28 mm, 29 mm, 30 mm, 31 mm, 32 mm, 33 mm, 34 mm, 35 mm, 36 mm, 37 mm, 38 mm, 39 mm, 40 mm, 41 mm, 42 mm, 43 mm, 44 mm, 45 mm, 46 mm, 47 mm, 48 mm, 49 mm, 50 mm, 51 mm, 52 mm, 53 mm, 54 mm, 55 mm, 56 mm, 57 mm, 58 mm, 59 mm, 60 mm, 61 mm, 62 mm, 63 mm, 64 mm, 65 mm, 66 mm, 67 mm, 68 mm, 69 mm, 70 mm, 71 mm, 72 mm, 73 mm, 74 mm, 75 mm, 76 mm, 77 mm, 78 mm, 79 mm, 80 mm, 81 mm, 82 mm, 83 mm, 84 mm, 85 mm, 86 mm, 87 mm, 88 mm, 89 mm, 90 mm, 91 mm, 92 mm, 93 mm, 94 mm, 95 mm, 96 mm, 97 mm, 98 mm, 99 mm, 100 mm, or a number or a range between any two of these values.

In some embodiments, the height or the thickness of the second layer 104s can be, can be about, can be at most, or can be at least, 10 µm, 20 µm, 30 µm, 40 µm, 50 µm, 60 µm, 70 µm, 80 µm, 90 µm, 100 µm, 110 µm, 120 µm, 130 µm, 140 µm, 150 µm, 160 µm, 170 µm, 180 µm, 190 µm, 200 µm, 210 µm, 220 µm, 230 µm, 240 µm, 250 µm, 260 µm, 270 µm, 280 µm, 290 µm, 300 µm, 310 µm, 320 µm, 330 µm, 340 µm, 350 µm, 360 µm, 370 µm, 380 µm, 390 µm, 400 µm, 410 µm, 420 µm, 430 µm, 440 µm, 450 µm, 460 µm, 470 µm, 480 µm, 490 µm, 500 µm, 510 µm, 520 µm, 530 µm, 540 µm, 550 µm, 560 µm, 570 µm, 580 µm, 590 µm, 600 µm, 610 µm, 620 µm, 630 µm, 640 µm, 650 µm, 660 µm, 670 µm, 680 µm, 690 µm, 700 µm, 710 µm, 720 µm, 730 µm, 740 µm, 750 µm, 760 µm, 770 µm, 780 µm, 790 µm, 800 µm, 810 µm, 820 µm, 830 µm, 840 µm, 850 µm, 860 µm, 870 µm, 880 µm, 890 µm, 900 µm, 910 µm, 920 µm, 930 µm, 940 µm, 950 µm, 960 µm, 970 µm, 980 µm, 990 µm, 1 mm, 2 mm, 3 mm, 4 mm, 5 mm, 6 mm, 7 mm, 8 mm, 9 mm, 10 mm, or a number or a range between any two of these values.

In some embodiments, the width (or length) of the array 104a layer can be a percentage of the width (or length) of the second layer 104s, such as 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, or a number or a range between any two of these values. For example, the width of the array 104a layer can be 95% of the width of the second layer 104s. In some embodiments, a surface area (width×length) of the array 104a layer can be a percentage of a surface area (width×length) of the second layer 104s, such as 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, or a number or a range between any two of these values. For example, for the surface of the second layer 104s that is in contact with the array 104a layer, 90% of the surface is in contact with the array 104a layer.

Mass Spectrometry Chip

In some embodiments, the mass spectrometry chip is a mass spectrometry chip for laser desorption/ionization MS. The laser desorption/ionization MS can be nanostructure-initiator mass spectrometry (NIMS), desorption/ionization on silicon (DIOS) MS, nanowire-assisted laser desorption/ionization (NALDI) MS, insulator nanostructure desorption ionization (INDI) MS, nanopost array laser desorption ionization (NAPA) MS, matrix-assisted laser desorption/ionization (MALDI) MS, surface-assisted laser desorption/ionization (SALDI) MS, surface-enhanced laser desorption/ionization (SELDI) MS, or a combination thereof. In some embodiments, the mass spectrometry chip is an indium tin oxide (ITO)-glass coated with a matrix compound. In some embodiments, the mass spectrometry chip is a NIMS chip.

The size of the MS chip can be different in different embodiments. For example, the MS chip can have a size of 2.5 cm (width)×2.5 cm (length) or 5 cm (width)×5 cm (length). In some embodiments, the width (or length or height) of the MS chip can be, can be about, can be at most, or can be at least, 0.1 cm, 0.2 cm, 0.3 cm, 0.4 cm, 0.5 cm, 0.6 cm, 0.7 cm, 0.8 cm, 0.9 cm, 1 cm, 1.1 cm, 1.2 cm, 1.3 cm, 1.4 cm, 1.5 cm, 1.6 cm, 1.7 cm, 1.8 cm, 1.9 cm, 2 cm, 2.1 cm, 2.2 cm, 2.3 cm, 2.4 cm, 2.5 cm, 2.6 cm, 2.7 cm, 2.8 cm, 2.9 cm, 3 cm, 3.1 cm, 3.2 cm, 3.3 cm, 3.4 cm, 3.5 cm, 3.6 cm, 3.7 cm, 3.8 cm, 3.9 cm, 4 cm, 4.1 cm, 4.2 cm, 4.3 cm, 4.4 cm, 4.5 cm, 4.6 cm, 4.7 cm, 4.8 cm, 4.9 cm, 5 cm, 5.1 cm, 5.2 cm, 5.3 cm, 5.4 cm, 5.5 cm, 5.6 cm, 5.7 cm, 5.8 cm, 5.9 cm, 6 cm, 6.1 cm, 6.2 cm, 6.3 cm, 6.4 cm, 6.5 cm, 6.6 cm, 6.7 cm, 6.8 cm, 6.9 cm, 7.0 cm, 7.1 cm, 7.2 cm, 7.3 cm, 7.4 cm, 7.5 cm, 7.6 cm, 7.7 cm, 7.8 cm, 7.9 cm, 8 cm, 8.1 cm, 8.2 cm, 8.3 cm, 8.4 cm, 8.5 cm, 8.6 cm, 8.7 cm, 8.8 cm, 8.9 cm, 9 cm, 9.1 cm, 9.2 cm, 9.3 cm, 9.4 cm, 9.5 cm, 9.6 cm, 9.7 cm, 9.8 cm, 9.9 cm, 10 cm, or a number or a range between any two of these values.

Sample Deposition

Figure 2A:
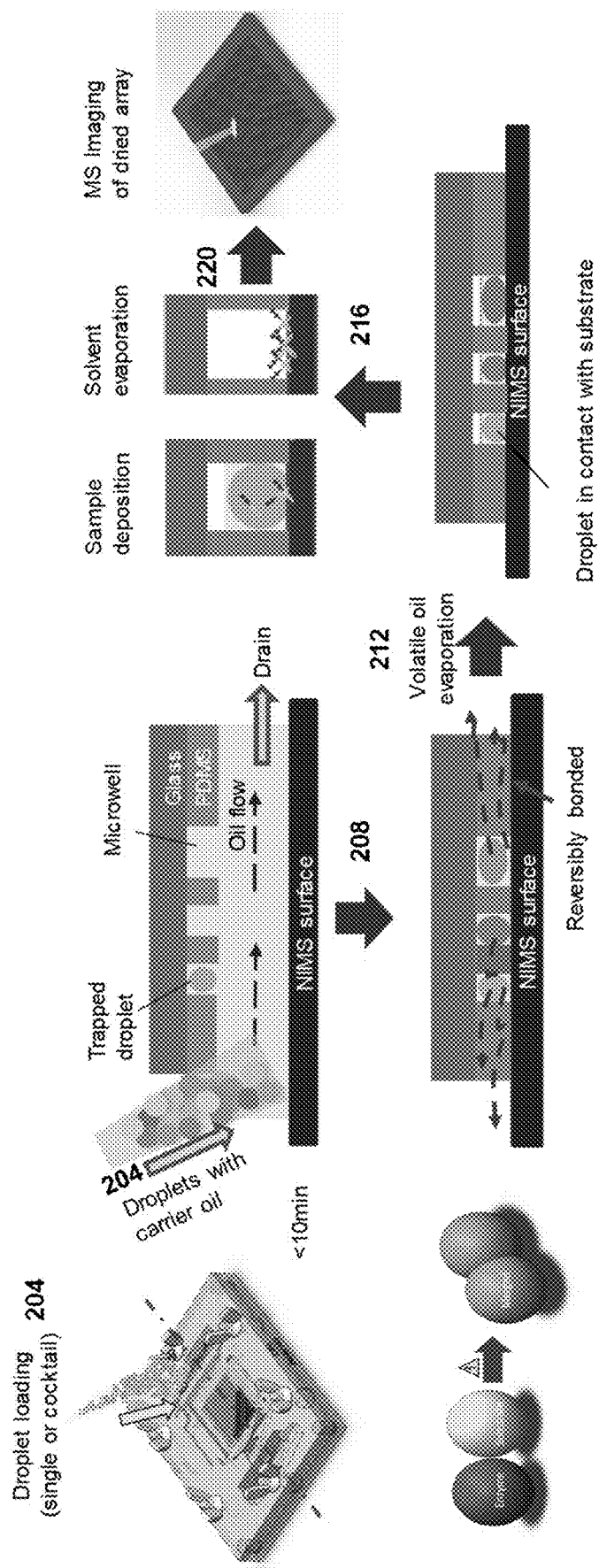
FIG. 2A shows rapid buoyancy-based droplet loading (e.g., 110 µm to 130 µm diameter) and array sample deposition. Upon completion of droplet entrapment, chip is sealed against NIMS surface for sample deposition. Volatile carrier oil and solvent evaporate, inducing sample deposition on surface. A reaction can occur inside a droplet before, when, and after the droplet is loaded onto the chip. A reaction can occur inside a droplet (e.g., a merged droplet or a droplet that is not merged from two or more droplets) after the chip is sealed against the MS surface. A reaction can occur when the oil and the solvent evaporate. A reaction can occur until the oil and the solvent evaporate completely (or mostly or almost completely). A reaction can occur after the content of the droplet is deposited onto the MS surface (e.g., for a period of time). A reaction can occur until or after the content of the droplet is deposited onto the MS surface.
Figure 2B:
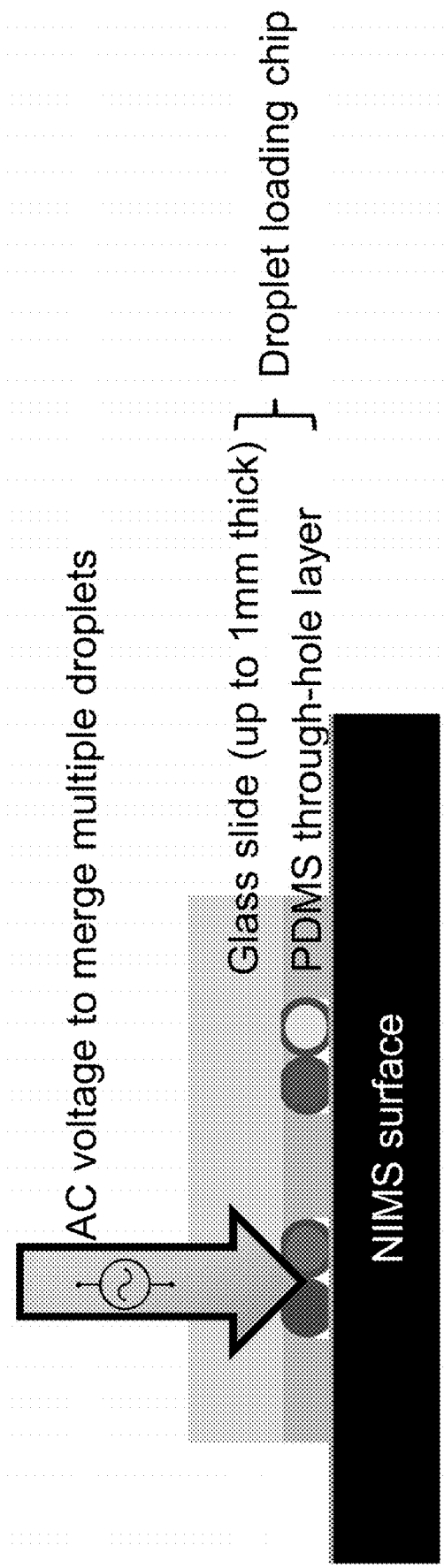
FIG. 2B shows that droplets can be merged by applying AC voltage through the PDMS/glass side, not through NIMS surface.

Disclosed herein include embodiments of a method for sample deposition on a mass spectrometry surface. FIG. 2A shows rapid buoyancy-based droplet loading and array sample deposition. A droplet cocktail with carrier oil can be introduced into the gap between the loading chip (e.g., a microfluidic chip) and MS (e.g., NIMS) surface. Due to density difference between the aqueous droplets and carrier oil, droplets float as the droplets travel and enter empty microwells above the droplets very quickly. After loading is complete, the loading chip is reversibly sealed against the MS surface, and multiple droplets can be merged by treating the surface with AC voltage (for example, using a portable AC voltage treater). In some embodiments, bright-field or fluorescence imaging can be performed after droplets are loaded into the wells and/or after droplets are merged. Volatile oil can gradually start evaporating after reversible sealing of the loading chip and the MS surface, and droplets can touch the MS surface and contents of the droplets (e.g., from samples being analyzed) can start being deposited on the MS surface. The droplet contents are physically confined by microwells. After complete evaporation of carrier oil, the dried array can be scanned using, for example, matrix-assisted laser desorption/ionization (MALDI) for MS imaging. FIG. 2B shows that droplets can be merged by applying AC voltage through the PDMS/glass side, not through NIMS surface.

In some embodiments, the method comprises: (a) generating a first plurality of droplets each comprising one or more first analytes. The method can comprise: (b) distributing droplets from the first plurality of droplets onto an array of wells in a microfluidic device (such as the device 100 described with reference to FIGS. 1A-1C) at 204. One, at least one, or each, of the wells of the array can be sized and/or shaped to capture one or more of the droplets from the first plurality of droplets. The method can comprise: (c) contacting a mass spectrometry (MS) surface of a MS chip with the well-opening surface of the array of wells comprising the distributed droplets from the first plurality of droplets at 208, thereby loading the one or more first analytes from the first plurality of droplets, or products thereof, onto the mass spectrometry surface at 216.

In some embodiments, the method comprises: (d) generating a second plurality of droplets each comprising one or more second analytes. The method can comprise (e) distributing droplets from the second plurality of droplets onto the array of wells at 204. Contacting the mass spectrometry surface with the well-opening surface of the array of wells can comprise contacting the mass spectrometry surface with the well-opening surface of the array of wells comprising the droplets from the first plurality of droplets and the droplets from the second plurality of droplets, thereby depositing the one or more first analytes from the first plurality of droplets, or products thereof, and the one or more second analytes from the second plurality of droplets, or products thereof, onto the mass spectrometry surface.

A reaction can occur inside a droplet after the droplet is generated and before the droplet is loaded onto the array of wells on the loading chip. A reaction can occur inside a droplet when and after the droplet is loaded onto the array of wells on the loading chip. A reaction can occur inside a droplet (e.g., a merged droplet or a droplet that is not merged from two or more droplets) after the array is sealed against the MS surface. A reaction can occur when the carrier fluid and/or the solvent and/or the oil of the solvent-in-oil emulsion or oil-in-solvent emulsion evaporate. A reaction can occur until the carrier fluid, the solvent, and/or the oil evaporate completely (or mostly or almost completely). A reaction can occur after the content of the droplet is deposited onto the MS surface (e.g., for a period of time). A reaction can occur until or after the content of the droplet is deposited onto the MS surface. The reaction time can depend on the time after the droplet is generated and before the droplet is loaded, the time for loading the droplet, the time for sealing the array against the MS surface, and/or the time for the carrier fluid, solvent, and/or oil to evaporate.

Screening Methods

Screening for an Enzyme Substrate

Disclosed herein include embodiments of a method for screening for an enzyme substrate. In some embodiments, the method comprises: (a) generating a first plurality of droplets each comprising one or more potential substrates of an enzyme and a second plurality of droplets each comprising the enzyme. The method can comprise: (b) distributing droplets from the first plurality of droplets and the second plurality of droplets onto an array of wells in a microfluidic device (e.g., the device 100 described with reference to FIGS. 1A-1C) at 204. One, at least one, or each, of the wells of the array can be sized and/or shaped to capture (i) one of the droplets from the first plurality of droplets and (ii) one of the droplets from the second plurality of droplets, thereby loading into one, at least one, or each, of the wells of the array zero, one, or two (or more) distributed droplets. The method can comprise merging droplets, if any, in one, at least one, or each, of the wells of the array into a merged droplet. An enzyme in a merged droplet can catalyze a substrate in the merged droplet to a product before the merged droplet and the carrier fluid evaporates. The method can comprise: (c) contacting a mass spectrometry (MS) surface of a mass spectrometry chip with a well-opening surface of the array of wells at 208, thereby depositing (i) the one or more potential substrates, or products thereof, if any, and (ii) the enzyme, if any, from the zero, one, or two distributed droplets in the one, at least one, or each, of the plurality of wells onto a location on the mass spectrometry surface corresponding to the well at 216. The method can comprise: (d) obtaining a mass spectrum of the one or more potential substrates, or products thereof, if any, and the enzyme, if any, deposited onto one, at least one, or each, of the locations on the mass spectrometry surface at 220. The method can comprise: (e) determining a potential substrate is a substrate of the enzyme using an absence of, or a decrease in, a first peak corresponding to the substrate. Alternatively, or additionally, the method can comprise: (e) determining a potential substrate is a substrate of the enzyme using a presence of, or an increase in, a second peak corresponding to a product (or second peaks corresponding to products) catalyzed from the substrate by the enzyme. Alternatively, or additionally, the method can comprise: (e) determining a potential substrate is a substrate of the enzyme using a third peak corresponding to the enzyme (e.g., the enzyme, or a barcode or a label identifying the enzyme) in a mass spectrum of the mass spectra obtained.

Screening Enzyme Activity

Disclosed herein include embodiments of a method for screening enzyme activity (e.g., screening for an enzyme capable of catalyzing a substrate to a product). In some embodiments, the method comprises: (a) generating a first plurality of droplets each comprising an identical substrate and a second plurality of droplets each comprising one or more potential enzymes capable of catalyzing the substrate to a product. The method can comprise: (b) distributing droplets from the first plurality of droplets and the second plurality of droplets onto an array of wells in a microfluidic device at 204. One, at least one, or each, of the wells of the array can be sized and/or shaped to capture (i) one of the droplets from the first plurality of droplets and (ii) one of the droplets from the second plurality of droplets, thereby loading into one, at least one, or each, of the wells of the array zero, one, or two distributed droplets. The method can comprise merging droplets, if any, in one, at least one, or each, of the wells of the array into a merged droplet. An enzyme in a merged droplet can catalyze a substrate in the merged droplet to a product before the merged droplet and the carrier fluid evaporates. The method can comprise: (c) contacting a mass spectrometry (MS) surface of a mass spectrometry chip with a well-opening surface of the array of wells at 208, thereby depositing (i) the substrate, or one or more products thereof, if any, and (ii) the zero, one, or two potential enzymes from the zero, one, or two distributed droplets in the one, at least one, or each, of the plurality of wells onto a location on the mass spectrometry surface corresponding to the well at 216. The method can comprise: (d) obtaining a mass spectrum of the substrate, or one or more products thereof, if any, and the zero, one, or two enzymes deposited onto one, at least one, or each, of the locations on the mass spectrometry surface at 220. The method can comprise: (e) determining a potential enzyme is an enzyme capable of catalyzing the substrate to a product using an absence of, or a decrease in, a first peak corresponding to the substrate. Alternatively, or additionally, the method can comprise: (e) determining a potential enzyme is an enzyme capable of catalyzing the substrate to a product using a presence of, or an increase in, a second peak corresponding to the product (or second peaks corresponding to the products). Alternatively, or additionally, the method can comprise: (e) determining a potential enzyme is an enzyme capable of catalyzing the substrate to a product using a third peak corresponding to the enzyme (e.g., the enzyme, or a barcode or a label identifying the enzyme) in a mass spectrum of the mass spectra obtained.

Screening Analytes

Disclosed herein include embodiments of a method for screening analytes (e.g., for screening an enzyme and a substrate of the enzyme in a reaction). In some embodiments, the method comprises: (a) generating a first plurality of droplets each comprising one or more first analytes (e.g., a substrate, or potential substrates) and a second plurality of droplets each comprising one or more second analytes (e.g., potential enzymes capable of catalyzing the substrate into a product, or an enzyme). The method can comprise: (b) distributing droplets from the first plurality of droplets and the second plurality of droplets onto an array of wells in a microfluidic device at 204. One, at least one, or each, of the wells of the array can be sized and/or shaped to capture (i) one of the droplets from the first plurality of droplets and (ii) one of the droplets from the second plurality of droplets, thereby loading into one, at least one, or each, of the wells of the array zero, one, or two distributed droplets. The method can comprise: (c) contacting a mass spectrometry (MS) surface of a mass spectrometry chip with a well-opening surface of the array of wells at 208, thereby depositing (i) the one or more first analytes, or products thereof, if any, and (ii) the one or more second analytes, or products thereof, if any, from the zero, one, or two distributed droplets in the one, at least one, or each, of the plurality of wells onto a location on the mass spectrometry surface corresponding to the well at 216. The method can comprise: (d) obtaining a mass spectrum of the one or more first analytes, or products thereof, if any, and the one or more second analytes, or products thereof, if any, deposited onto one, at least one, or each, of the locations on the mass spectrometry surface at 220. The method can comprise: (e) determining a first analyte and a second analyte are components of a reaction using a first peak, or absence thereof, corresponding to the first analyte, and/or a second peak, or absence thereof, corresponding to the second analyte in a mass spectrum of the mass spectra obtained.

Screening an Analyte

Disclosed herein include embodiments of a method for screening an analyte (or one or more analytes). In some embodiments, the method comprises: distributing droplets from a first plurality of droplets each potentially comprising one or more first analytes onto an array of wells at 204, thereby loading into one, at least one, or each, of the wells of the array one or more distributed droplets. The method can comprise: contacting a mass spectrometry (MS) surface of a mass spectrometry chip with a well-opening surface of the array of wells at 208, thereby depositing the one or more first analytes, if any, in the one, at least one, or each, of the plurality of wells onto a location on the mass spectrometry surface corresponding to the well at 216. The method can comprise: obtaining a mass spectrum of the one or more first analytes, if any, deposited onto one, at least one, or each, of the locations on the mass spectrometry surface from a droplet of the first plurality of droplets at 220. The method can comprise: determining a presence, or an absence, of a first analyte of the one or more analytes in one, at least one, or each, of the droplets from the plurality of first droplets using a presence, or an absence, of a first peak corresponding to the first analyte in a mass spectrum of the mass spectra obtained from a location of the locations on the mass spectrometry surface onto which a content of the droplet is deposited. In some embodiments, one, at least one, or each, of the wells of the array is sized and/or shaped to capture one or more of the droplets from the first plurality of droplets. Alternatively, or additionally, the method can comprise: for one, at least one, or each, of the mass spectra obtained, determining a presence, or an absence, of a first analyte of the one or more analytes in one, at least one, or each, of the droplets from the plurality of first droplets using a presence, or an absence, of a first peak corresponding to the first analyte in the mass spectrum of the mass spectra obtained from a location of the locations on the mass spectrometry surface onto which a content of the droplet is deposited.

In some embodiments, determining the presence, or the absence, of the first analyte comprises determining an increase, or a decrease, of the first analyte in one, at least one, or each, of the droplets from the plurality of first droplets using an increase, or a decrease, of the first peak corresponding to the first analyte in the mass spectrum obtained from the location on the mass spectrometry surface onto which the content of the droplet is deposited. The method can comprise determining a stability of the one or more first analytes based on the presence, the absence, the increase in, or the decrease in, the first peak corresponding to the first analyte in the mass spectrum.

Screening a Reaction

Disclosed herein include embodiments of a method for screening reactions. In some embodiments, the method comprises: (a) generating a first plurality of droplets each comprising one or more potential reaction partners (e.g., one or more first analytes, such as enzymes or substrates) of an analyte (e.g., a second analyte, such as an enzyme or a substrate) and a second plurality of droplets each comprising the analyte. In some embodiments, the method comprises: (a) generating a first plurality of droplets each comprising an analyte and a second plurality of droplets each comprising one or more potential reaction partners of the analyte. The method can comprise: (b) distributing droplets from the first plurality of droplets and the second plurality of droplets onto an array of wells in a microfluidic device, thereby loading into one, at least one, or each, of the wells of the array zero, one, or two distributed droplets at 204. The method can comprise: (c) contacting a mass spectrometry (MS) surface of a mass spectrometry chip with a well-opening surface of the array of wells at 208, thereby depositing (i) the one or more potential reaction partners, or products thereof, if any, and (ii) the analyte, if any, from the zero, one, or two distributed droplets in the one, at least one, or each, of the plurality of wells onto a location on the mass spectrometry surface corresponding to the well at 216. The method can comprise: (d) obtaining a mass spectrum of the one or more potential reaction partners, or products thereof, if any, and the analyte, or a product thereof, if any, deposited onto one, at least one, or each, of the locations on the mass spectrometry surface. The method can comprise: (e) determining a potential reaction partner is a reaction partner of the analyte using an absence of, or a decrease in, a first peak corresponding to the substrate, and/or an absence of, or a decrease in, a second peak corresponding to the analyte in a mass spectrum of the mass spectra obtained. Alternatively, or additionally, the method can comprise: (e) determining a potential reaction partner is a reaction partner of the analyte using an absence of, or a decrease in, a first peak corresponding to the substrate, a presence of, or an increase in, the first peak corresponding to the substrate, an absence of, or a decrease in, a second peak corresponding to the analyte, and/or a presence of, or an increase in, the second peak corresponding to the analyte in a mass spectrum of the mass spectra obtained. Alternatively, or additionally, the method can comprise: for one, at least one, or each of the mass spectra obtained, (e) determining a potential reaction partner is a reaction partner of the analyte using an absence of, or a decrease in, a first peak corresponding to the substrate, a presence of, or an increase in, the first peak corresponding to the substrate, an absence of, or a decrease in, a second peak corresponding to the analyte, and/or a presence of, or an increase in, the second peak corresponding to the analyte in the mass spectrum of the mass spectra obtained.

In some embodiments, at least two of the droplets from the first plurality of droplets comprises one potential reaction partner in different concentrations, or comprise different buffer conditions. At least two of the droplets from the second plurality of droplets comprise the analyte in different concentrations or comprise different buffer conditions. In some embodiments, at least two of the droplets from the first plurality of droplets comprises one first analyte in different concentrations, or comprise different buffer conditions. At least two of the droplets from the second plurality of droplets comprise one second analyte in different concentrations or comprise different buffer conditions. In some embodiments, at least two of the droplets from the first plurality of droplets comprises one enzyme (or substrate) in different concentrations, or comprise different buffer conditions. At least two of the droplets from the second plurality of droplets comprise one substrate (or one enzyme) in different concentrations or comprise different buffer conditions.

In some embodiments, the method comprises (d) generating n pluralities of droplets each comprising one or more nth analytes, where n is a positive integer, such as 2, 3, 4, 5, 6, 7, 8, 9, 10, 20, 30, 40, 50, 60, 70, 80, 90, 100, 200, 300, 400, 500, 600, 700, 800, 900, 1000, or more. Each droplet can include, for example, 1, 2, 3, 4, 5, 6, 7, 8, 9, 10, 20, 30, 40, 50, 60, 70, 80, 90, 100, 200, 300, 400, 500, 600, 700, 800, 900, 1000, or more, analytes (or components, such as salts, buffers). The method can comprise (e) distributing droplets form the n pluralities of droplets into the array of wells. In some embodiments, the method comprises (d) generating a 3rd plurality, . . . , and a nth plurality of droplets each comprising one or more 3rd, 4th, 5th, . . . , or nth analytes, respectively, where n is a positive integer greater than 5, such as 6, 7, 8, 9, 10, 20, 30, 40, 50, 60, 70, 80, 90, 100, 200, 300, 400, 500, 600, 700, 800, 900, 1000, or more. The method can comprise (e) distributing droplets from the 3rd plurality, the 4th plurality, the 5th plurality, . . . , and/or the nth plurality of droplets onto the array of wells and/or into wells of the array of wells.

In some embodiments, one, at least one, or each, of the first plurality of droplets each comprises an identical first analyte, and two droplets of the second plurality of droplets comprise different second analytes or an identical second analyte at different concentrations. In some embodiments, one, at least one, or each, of the second plurality of droplets comprises an identical second analyte, and two droplets of the first plurality of droplets comprise different first analytes or an identical first analyte at different concentrations. In some embodiments, the first analyte is a drug and the second analyte is an enzyme capable of metabolizing the drug to a product (or a metabolite), or the first analyte is an enzyme substrate and the second substrate is an enzyme capable of converting the enzyme substrate to a product. In some embodiments, the second analyte is a drug and the first analyte is an enzyme capable of metabolizing the drug to a product (or a metabolite), or the second analyte is an enzyme substrate and the first substrate is an enzyme capable of converting the enzyme substrate to a product.

In some embodiments, the method comprises: generating a mixture of the first plurality of droplets and the second plurality of droplets (or a mixture of n pluralities of droplets). The droplets from the first plurality of droplets and the droplets form the second plurality of droplets (or the droplets from the n pluralities of droplets) can be loaded onto the array of wells together by distributing onto the array of wells the mixture of the first plurality of droplets and the second plurality of droplets (or the n pluralities of droplets). In some embodiments, the droplets from the first plurality of droplets and the droplets form the second plurality of droplets (or the droplets from the n pluralities of droplets) are loaded into wells of the array of wells sequentially.

Droplet Generation

In some embodiments, the droplets can be generated using microfluidic approaches. The droplets described herein include emulsion compositions (or mixtures of two or more immiscible fluids). The term "emulsion," as used herein, can refer to a mixture of immiscible liquids (such as oil and water). Oil-phase and/or water-in-oil emulsions allow for the compartmentalization of reaction mixtures within aqueous droplets. The emulsions can comprise aqueous droplets within a continuous oil phase. The emulsions provided herein can be oil-in-water emulsions, wherein the droplets are oil droplets within a continuous aqueous phase. The droplets provided herein are designed to prevent mixing between compartments, with each compartment protecting its contents from evaporation and coalescing with the contents of other compartments.

The oil phase can comprise a fluorinated base oil which can be additionally stabilized by combination with a fluorinated surfactant such as a perfluorinated polyether. In some cases, the base oil can be one or more of HFE 7500, FC-40, FC-43, FC-70, or another common fluorinated oil.

Distributing Droplets

In some embodiments, distributing the droplets from the first plurality of droplets onto the array of wells at 208 comprises flowing the first plurality of droplets in a carrier fluid through a channel formed by a space between the well-opening surface of the array of wells and the mass spectrometry surface.

The carrier fluid can be an oil and/or a non-ionic surfactant. The carrier fluid can comprise a fluorinated base oil which can be additionally stabilized by combination with a fluorinated surfactant such as a perfluorinated polyether. In some cases, the base oil can be one or more of HFE 7500, FC-40, FC-43, FC-70, or another common fluorinated oil. In some embodiments, distributing the droplets from the first plurality of droplets onto the array of wells comprises distributing the droplets from the first plurality of droplets into wells of the array.

In some embodiments, distributing the droplets from the second plurality of droplets onto the array of wells at 208 comprises flowing the second plurality of droplets in a carrier fluid through the channel formed by the space between the well-opening surface of the array of wells and the mass spectrometry surface. Distributing the droplets from the second plurality of droplets onto the array of wells can comprise distributing the droplets from the second plurality of droplets into wells of the array.

In some embodiments, distributing the droplets from the first and second plurality of droplets onto the array of wells at 208 comprises introducing both one droplet from the first plurality of droplets and one droplet from the second plurality of droplets into at least one well of the array of wells. In some embodiments, distributing droplets from the first and/or second plurality of droplets comprises randomly distributing the droplets to the array of wells.

Array and Wells of Array

In some embodiments, the array of wells is positioned with the well-opening surface facing down. The mass spectrometry chip can be positioned with mass spectrometry surface facing up. In some embodiments, the array of wells is positioned with the well-opening surface facing up. The mass spectrometry chip can be positioned with mass spectrometry surface facing down.

In some embodiments, one or more of the wells in the array of wells are each sized and/or shaped to capture two or more of the droplets from the first plurality of droplets or two or more droplets from the second plurality of droplets. In some embodiments, one, at least one, or each, of the wells of the array is sized and/or shaped to capture (i) at most one of the droplets from the first plurality of droplets, and (ii) at most one of the droplets from the second plurality of droplets when the droplet from the first plurality of droplets is captured in the well of the array. The droplets from the first plurality of droplets can be larger than the droplets from the second plurality of droplets. Distributing the droplets from the first plurality of droplets can occur before distributing the droplets from the second plurality of droplets, thereby one, at least one, or each, of the wells of the array comprises: (i) none of the droplets from the first plurality of droplets and none of the droplets from the second plurality of droplets, (ii) one of the droplets from the first plurality of droplets and none of the droplets from the second plurality of droplets, (iii) one of the droplets from the first plurality of droplets and one of the droplets from the second plurality of droplets, or (iv) at least one of the droplets from the second plurality of droplets.

The number of droplets that a well of the array can capture can be different in different implementations. In some embodiments, the number of droplets that a well of an array of the array can capture can be, be about, be at least, or be at most, 1, 2, 3, 4, 5, 6, 7, 8, 9, 10, 11, 12, 13, 14, 15, 16, 17, 18, 19, 20, 30, 40, 50, 60, 70, 80, 90, 100, or a number or a range between any two of these values.

Wells Occupancy

In some embodiments, at least 50%, at least 75%, or at least 90% of the wells of the array of wells each comprises both one droplet from the first plurality of droplets and one droplet from the second plurality of droplets. In some embodiments, at least, or at least about, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, each comprises one droplet from the first plurality of droplets (or one droplet from the first plurality of droplets). In some embodiments, at least, or at least about, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, each comprises one droplet from the first plurality of droplets and one droplet from the first plurality of droplets.

Droplets

In some embodiments, the droplets from the first plurality of droplets, the droplets from the second plurality of droplets, or both, have an average diameter of about 10 µm to about 400 µm, about 20 µm to about 200 µm, or about 70 µm to about 150 µm. The average diameter can be, be about, be at least, or be at most, 1 µm, 2 µm, 3 µm, 4 µm, 5 µm, 6 µm, 7 µm, 8 µm, 9 µm, 10 µm, 10 µm, 20 µm, 30 µm, 40 µm, 50 µm, 60 µm, 70 µm, 80 µm, 90 µm, 100 µm, 110 µm, 120 µm, 130 µm, 140 µm, 150 µm, 160 µm, 170 µm, 180 µm, 190 µm, 200 µm, 210 µm, 220 µm, 230 µm, 240 µm, 250 µm, 260 µm, 270 µm, 280 µm, 290 µm, 300 µm, 310 µm, 320 µm, 330 µm, 340 µm, 350 µm, 360 µm, 370 µm, 380 µm, 390 µm, 400 µm, 410 µm, 420 µm, 430 µm, 440 µm, 450 µm, 460 µm, 470 µm, 480 µm, 490 µm, 500 µm, or a number or a range between any two of these values.

In some embodiments, the droplets from the first plurality of droplets, the droplets from the second plurality of droplets, or both, have a volume of, of about, of at least, or of at most, 1 pl, 2 pl, 3 pl, 4 pl, 5 pl, 6 pl, 7 pl, 8 pl, 9 pl, 10 pl, 20 pl, 30 pl, 40 pl, 50 pl, 60 pl, 70 pl, 80 pl, 90 pl, 100 pl, 110 pl, 120 pl, 130 pl, 140 pl, 150 pl, 160 pl, 170 pl, 180 pl, 190 pl, 200 pl, 210 pl, 220 pl, 230 pl, 240 pl, 250 pl, 260 pl, 270 pl, 280 pl, 290 pl, 300 pl, 310 pl, 320 pl, 330 pl, 340 pl, 350 pl, 360 pl, 370 pl, 380 pl, 390 pl, 400 pl, 410 pl, 420 pl, 430 pl, 440 pl, 450 pl, 460 pl, 470 pl, 480 pl, 490 pl, 500 pl, 510 pl, 520 pl, 530 pl, 540 pl, 550 pl, 560 pl, 570 pl, 580 pl, 590 pl, 600 pl, 610 pl, 620 pl, 630 pl, 640 pl, 650 pl, 660 pl, 670 pl, 680 pl, 690 pl, 700 pl, 710 pl, 720 pl, 730 pl, 740 pl, 750 pl, 760 pl, 770 pl, 780 pl, 790 pl, 800 pl, 810 pl, 820 pl, 830 pl, 840 pl, 850 pl, 860 pl, 870 pl, 880 pl, 890 pl, 900 pl, 910 pl, 920 pl, 930 pl, 940 pl, 950 pl, 960 pl, 970 pl, 980 pl, 990 pl, 1000 pl, 2 nl, 3 nl, 4 nl, 5 nl, 6 nl, 7 nl, 8 nl, 9 nl, 10 nl, 20 nl, 30 nl, 40 nl, 50 nl, 60 nl, 70 nl, 80 nl, 90 nl, 100 nl, 110 nl, 120 nl, 130 nl, 140 nl, 150 nl, 160 nl, 170 nl, 180 nl, 190 nl, 200 nl, 210 nl, 220 nl, 230 nl, 240 nl, 250 nl, 260 nl, 270 nl, 280 nl, 290 nl, 300 nl, 310 nl, 320 nl, 330 nl, 340 nl, 350 nl, 360 nl, 370 nl, 380 nl, 390 nl, 400 nl, 410 nl, 420 nl, 430 nl, 440 nl, 450 nl, 460 nl, 470 nl, 480 nl, 490 nl, 500 nl, 510 nl, 520 nl, 530 nl, 540 nl, 550 nl, 560 nl, 570 nl, 580 nl, 590 nl, 600 nl, 610 nl, 620 nl, 630 nl, 640 nl, 650 nl, 660 nl, 670 nl, 680 nl, 690 nl, 700 nl, 710 nl, 720 nl, 730 nl, 740 nl, 750 nl, 760 nl, 770 nl, 780 nl, 790 nl, 800 nl, 810 nl, 820 nl, 830 nl, 840 nl, 850 nl, 860 nl, 870 nl, 880 nl, 890 nl, 900 nl, 910 nl, 920 nl, 930 nl, 940 nl, 950 nl, 960 nl, 970 nl, 980 nl, 990 nl, 1000 nl, or a number or a range between any two of these values.

The percentage of the droplets from the first plurality of droplets, the droplets from the second plurality of droplets, or both, have a particular average diameter, or volume, can be, be about, be at least, or be at most, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, or a number or a range between any two of these values.

The number of analytes in a droplet can be different in different implementations. In some embodiments, the number of analytes in one, at least one, or each of the first plurality of droplets and/or the second plurality of droplets is 1, 2, 3, 4, 5, 6, 7, 8, 9, 10, 11, 12, 13, 14, 15, 16, 17, 18, 19, 20, 30, 40, 50, 60, 70, 80, 90, 100, or a number or a range between any two of these values.

The number of droplets from the first plurality of droplets and/or the second plurality of droplets with unique substrates and/or enzymes can be different in different implementations. In some embodiments, the droplets from the first plurality of droplets and/or the second plurality of droplets comprise 1, 2, 3, 4, 5, 6, 7, 8, 9, 10, 11, 12, 13, 14, 15, 16, 17, 18, 19, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, or a number or a range between any two of these values, different substrates (e.g., drugs or biomass). In some embodiments, the droplets from the first plurality of droplets and/or the second plurality of droplets comprise an identical substrate. In some embodiments, the droplets from the first plurality of droplets and/or the second plurality of droplets comprise 1, 2, 3, 4, 5, 6, 7, 8, 9, 10, 11, 12, 13, 14, 15, 16, 17, 18, 19, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, or a number or a range between any two of these values, different enzymes. In some embodiments, the droplets from the first plurality of droplets and/or the second plurality of droplets comprise an identical enzyme.

Merging Droplets

In some embodiments, the systems, devices, and methods disclosed herein can be used for array (or load) droplets without merging (or mixing) the droplets after loading them onto the array. In some embodiments, the method comprises merging the one droplet from the first plurality of droplets and the one droplet from the second plurality of droplets in the well where the two droplets are introduced into. In some embodiments, with the thinner PDMS layer on glass, droplets can be merged by applying AC voltage through the PDMS/glass side, not through NIMS surface (FIGS. 1C and 2B). For example, Merging the one droplet from the first plurality of droplets and the one droplet from the second plurality of droplets in the well where the two droplets are introduced into can comprise applying a voltage to the droplet loading chip (e.g., via a window 136w for applying an alternating current (AC) as shown in FIG. 1C). In some embodiments, merging the one droplet from the first plurality of droplets and the one droplet from the second plurality of droplets in the well where the two droplets are introduced into can comprise applying a voltage to the mass spectrometry chip. The voltage applied can be different in different embodiments. In some embodiments, the voltage applied is, is about, is at least, or is at most, 1 Volts (V), 10 V, 20 V, 30 V, 40 V, 50 V, 60 V, 70 V, 80 V, 90 V, 100 V, 110 V, 120 V, 130 V, 140 V, 150 V, 160 V, 170 V, 180 V, 190 V, 200 V, 210 V, 220 V, 230 V, 240 V, 250 V, 260 V, 270 V, 280 V, 290 V, 300 V, 310 V, 320 V, 330 V, 340 V, 350 V, 360 V, 370 V, 380 V, 390 V, 400 V, 410 V, 420 V, 430 V, 440 V, 450 V, 460 V, 470 V, 480 V, 490 V, 500 V, 510 V, 520 V, 530 V, 540 V, 550 V, 560 V, 570 V, 580 V, 590 V, 600 V, 610 V, 620 V, 630 V, 640 V, 650 V, 660 V, 670 V, 680 V, 690 V, 700 V, 710 V, 720 V, 730 V, 740 V, 750 V, 760 V, 770 V, 780 V, 790 V, 800 V, 810 V, 820 V, 830 V, 840 V, 850 V, 860 V, 870 V, 880 V, 890 V, 900 V, 910 V, 920 V, 930 V, 940 V, 950 V, 960 V, 970 V, 980 V, 990 V, 1 kV, 2 kV, 3 kV, 4 kV, 5 kV, 6 kV, 7 kV, 8 kV, 9 kV, 10 kV, 11 kV, 12 kV, 13 kV, 14 kV, 15 kV, 16 kV, 17 kV, 18 kV, 19 kV, 20 kV, 21 kV, 22 kV, 23 kV, 24 kV, 25 kV, 26 kV, 27 kV, 28 kV, 29 kV, 30 kV, 31 kV, 32 kV, 33 kV, 34 kV, 35 kV, 36 kV, 37 kV, 38 kV, 39 kV, 40 kV, 41 kV, 42 kV, 43 kV, 44 kV, 45 kV, 46 kV, 47 kV, 48 kV, 49 kV, 50 kV, 51 kV, 52 kV, 53 kV, 54 kV, 55 kV, 56 kV, 57 kV, 58 kV, 59 kV, 60 kV, 61 kV, 62 kV, 63 kV, 64 kV, 65 kV, 66 kV, 67 kV, 68 kV, 69 kV, 70 kV, 71 kV, 72 kV, 73 kV, 74 kV, 75 kV, 76 kV, 77 kV, 78 kV, 79 kV, 80 kV, 81 kV, 82 kV, 83 kV, 84 kV, 85 kV, 86 kV, 87 kV, 88 kV, 89 kV, 90 kV, 91 kV, 92 kV, 93 kV, 94 kV, 95 kV, 96 kV, 97 kV, 98 kV, 99 kV, 100 kV, 200 kV, 300 kV, 400 kV, 500 kV, 600 kV, 700 kV, 800 kV, 900 kV, or a number or a range between any two of these values.

In some embodiments, one, at least one, or each of the plurality (e.g., the first, second plurality, or nth plurality) of droplets is merged from 2, 3, 4, 5, 6, 7, 8, 9, 10, 20, 30, 40, 50, 60, 70, 80, 90, 100, or more droplets. The merged droplet can be generated prior to being loaded onto the array of wells. The merged droplet can be generated after the droplets being merged are loaded onto the array of microwells (e.g., loaded into a microwell of the array).

Contacting Array with Mass Spectrometry Surface

In some embodiments, contacting the well-opening surface of the array of wells with the mass spectrometry surface comprises sealing the well-opening surface of the array of wells with the mass spectrometry surface via a reversible sealing mechanism. The reversible sealing mechanism can comprise a top clamp located above the array of wells and a bottom clamp on which the mass spectrometry chip is placed. The top clamp can be a clamping plate located above the side of the array of wells opposite of the well-opening surface of the array of wells, and the bottom clamp can be a clamping plate located below a side of the mass spectrometry chip opposite of the mass spectrometry surface.

In some embodiments, the droplets from the first and/or second plurality of droplets rise (see FIG. 2A for an example) or sink via buoyancy from the space between the well-opening surface of the array of wells and the mass spectrometry surface into the wells. In some embodiments, the droplets from the first plurality of droplets, the droplets from the second plurality of droplets, or both are in a solvent-in-oil emulsion. The oil in the solvent-in-oil emulsion can be a fluorinated oil. The solvent in the solvent-in-oil emulsion can be water, a buffer solution, a salt solution, an organic solvent, or any combination thereof.

In some embodiments, the method comprises evaporating the carrier fluid in which the droplets are distributed from the mass spectrometry surface at 212. In some embodiments, the method comprises evaporating the droplets (e.g., the solvent and/or oil of droplets comprising solvent-in-oil emulsions or oil-in-solvent emulsions) from the mass spectrometry surface at 216. The carrier fluid and/or the droplets can be evaporated in, in about, in at least, or in at most, 10 mins, 20 mins, 30 mins, 40 mins, 50 mins, 60 mins, 2 hrs, 3 hrs, 4 hrs, 5 hrs, 6 hrs, 7 hrs, 8 hrs, 9 hrs, 10 hrs, 11 hrs, 12 hrs, 13 hrs, 14 hrs, 15 hrs, 17 hrs, 18 hrs, 19 hrs, 20 hrs, 21 hrs, 22 hrs, 23 hrs, 24 hrs, or a number or a range between any two of these values. In some embodiments, the method comprises: unsealing the well-opening surface of the array of wells with the mass spectrometry surface after the carrier fluid and the droplets are evaporated (e.g., complete, almost complete, or partial evaporation).

Detection

In some embodiments, the droplets from the first plurality of droplets, the droplets from the second plurality of droplets, or both comprise a detectable barcode that identifies the one or more first or second analytes in a given droplet. The detectable barcode can comprise an optically detectable label, a label detectable by mass spectrometry, a nucleotide label, a peptide label, or a combination thereof. The optically detectable label can be a fluorophore. The label detectable by mass spectrometry can be a lanthanide-chelator complex. Using lanthanide-chelator complexes to track and identify analytes and concentrations of analytes has been described in US 2017/0348665, the content of which is incorporated herein by reference in its entirety. In some embodiments, a protein (e.g., an enzyme) can be associated with (such as coupled to by, for example, conjugation, covalent bonding, or non-covalent interaction) a peptide label or a nucleotide label. The detectable barcode can be selected from a set of, of about, of at least, or of at most 5, 6, 7, 8, 9, 10, 20, 30, 40, 50, 60, 70, 80, 90, 100, 200, 300, 400, 500, 600, 700, 800, 900, 1000, or a number or a range between any two of these values, distinct barcodes.

Figure 3A:
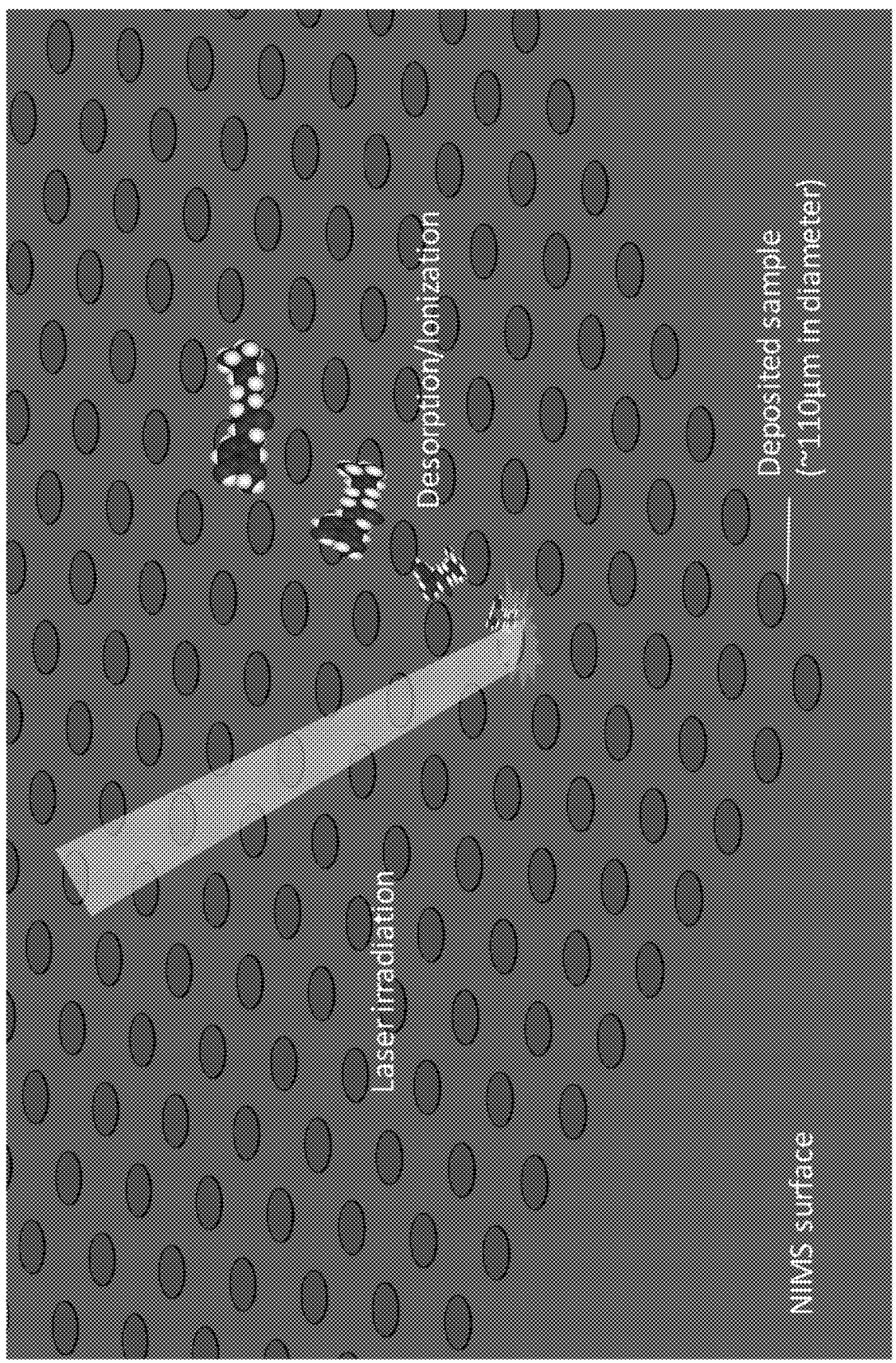
FIGS. 3A-3B show nanostructure-initiator mass spectrometry deposited sample array.
Figure 3B:
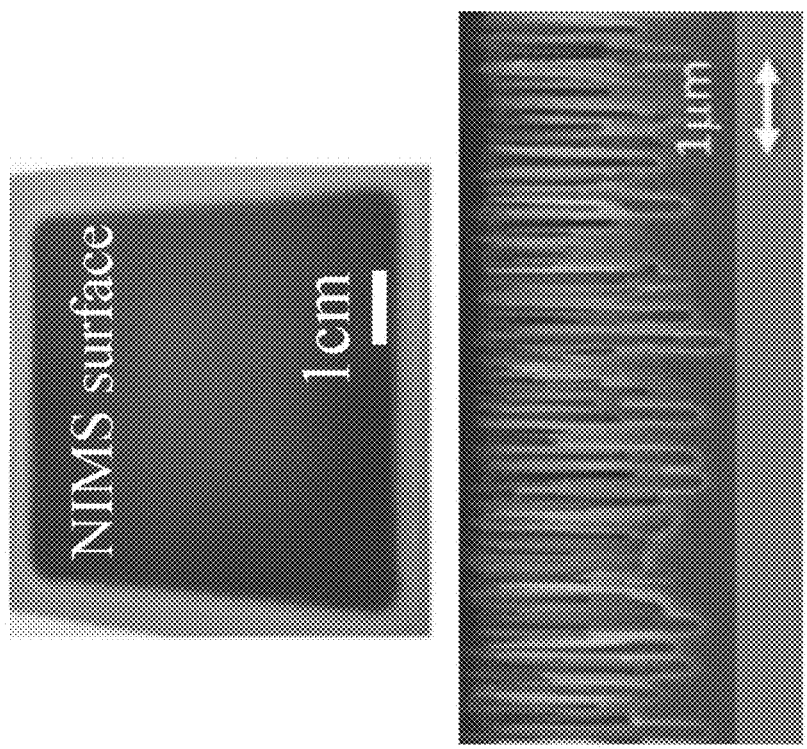

In some embodiments, the method comprises identifying the one or more first or second analytes, or products thereof, deposited onto the mass spectrometry surface using mass spectrometry. The mass spectrometry can be laser desorption/ionization MS. The laser desorption/ionization MS can be nanostructure-initiator mass spectrometry (NIMS), desorption/ionization on silicon (DIOS) MS, nanowire-assisted laser desorption/ionization (NALDI) MS, insulator nanostructure desorption ionization (INDI) MS, nanopost array laser desorption ionization (NAPA) MS, matrix-assisted laser desorption/ionization (MALDI) MS, surface-assisted laser desorption/ionization (SALDI) MS, surface-enhanced laser desorption/ionization (SELDI) MS, or a combination thereof. FIGS. 3A-3B show nanostructure-initiator mass spectrometry deposited sample array. FIG. 3A shows an illustration of the laser irradiation on NIMS surface resulting in desorption of sample. FIG. 3B shows a photograph of NIMS surface (5 cm×5 cm) with a zoomed-in scanning electron microscope (SEM) image of nanostructured surface.

Applications

In some embodiments, the systems, devices, and methods disclosed herein can be used for enzyme screening. In some embodiments, the systems, devices, and methods disclosed herein can be used to array (e.g., deposit) small molecules onto a MS surface (e.g., drugs), which can in turn be characterized using mass spectrometry. The systems, devices, and methods can be used for clinical applications, for example detecting drugs of abuse from urine samples arrayed in droplets, or screening drug stability under diverse buffer conditions. The systems, devices, and methods can be used to prototype biosynthetic pathways for synthetic biology by mixing together different libraries of enzymes etc. The systems, devices, and methods can be used to array microbes to study their interactions, for example, by screening for novel secondary metabolites (e.g., antibiotics) produced by microbes when the microbes interact.

In some embodiments, the systems, methods, and devices disclosed herein can be used to screen huge libraries (e.g., an enzyme library, and a chemical or compound library) using mass spectrometry. The systems, methods, and devices can be used to study, or investigate, chemical synthesis, enzyme reactions, effects of buffer conditions, solubility, interactions (e.g., between organisms), in vitro biochemistry, synthetic biology (e.g., best substrates to produce target molecules).

Samples and Analytes

The types of analytes that can be deposited to a mass spectrometry and/or to analyzed using the methods and systems described herein can vary. For example, the analytes include, for example, amino acids, carbohydrates, fatty acids, peptides, sugars, lipids, nucleic acids, polynucleotides, glycosaminoglycans, polypeptides, or proteins. In some embodiments, the analyte is a drug. In some embodiments, the analyte is an enzyme. The analytes can be synthetic, isolated, recombinant, or present within a metabolic pathway within a living system.

In some embodiments, the one or more first analytes from the first plurality of droplets, the one or more second analytes from the second plurality of droplets, or both, comprise a protein, a polypeptide, a peptide, a nucleic acid, a lipid, a carbohydrate, a small molecule drug, a cell, or any combination thereof. In some embodiments, the one or more first analytes from the first plurality of droplets, the one or more second analytes from the second plurality of droplets, or both, comprise an enzyme, a dye, an enzymatic substrate, a metabolite, or any combination thereof.

In some embodiments, the one or more first analytes from the first plurality of droplets comprise an enzyme, and the one or more second analytes from the second plurality of droplets comprise a possible enzymatic substrate of the enzyme, or the one or more second analytes from the second plurality of droplets comprise an enzymatic substrate and the one or more first analytes from the first plurality of droplets comprise an enzyme being screened for a capability of converting the enzymatic substrate into a product.

In some embodiments, the substrate is a drug, and the enzyme is capable of metabolizing the drug to a product (or a metabolite). In some embodiments, the substrate is a biomass-related substrate. In some embodiments, the method and device disclosed herein can be used for drug metabolism study, e.g., by screening drugs against enzymes. In some embodiments, the method and device disclosed herein can be used for biomass deconstruction and synthetic biology, e.g., by screening biomass against enzymes.

In some embodiments, the method comprises generating the first plurality of droplets (or nth plurality of droplets) each comprising the one or more first analytes. The method can comprise generating the first plurality of droplets comprises generating the first plurality of droplets from a library of samples. The library of samples can comprise a library of first analytes. The library of first analytes can comprise a library of enzymes, a library of drugs, a library of metabolites, a library of antibiotics, or a combination thereof. Generating the first plurality of droplets can comprise generating a droplet of the first plurality of droplets from a sample. The method can comprise determining a presence, or an absence, of the first analyte in the sample using the presence, or the absence, of the first analyte determined. The sample can comprise a clinical sample, a soil sample, an air sample, an environmental sample, a cell culture sample, a bone marrow sample, a rainfall sample, a fallout sample, a sewage sample, a ground water sample, an abrasion sample, an archaeological sample, a food sample, a blood sample, a serum sample, a plasma sample, a urine sample, a stool sample, a semen sample, a lymphatic fluid sample, a cerebrospinal fluid sample, a nasopharyngeal wash sample, a sputum sample, a mouth swab sample, a throat swab sample, a nasal swab sample, a bronchoalveolar lavage sample, a bronchial secretion sample, a milk sample, an amniotic fluid sample, a biopsy sample, a cancer sample, a tumor sample, a tissue sample, a cell sample, a cell culture sample, a cell lysate sample, a virus culture sample, a nail sample, a hair sample, a skin sample, a forensic sample, an infection sample, a nosocomial infection sample, a production sample, a drug preparation sample, a biological molecule production sample, a protein preparation sample, a lipid preparation sample, a carbohydrate preparation sample, a space sample, an extraterrestrial sample or a combination thereof.

In some embodiments, the one or more first analytes comprise a protein, an enzyme, an antibody, an immunogen, an antigen, a drug, a metabolite, an antibiotic, a nucleic acid, a lipid, a carbohydrate, a cell, a microbial cell, or a combination thereof. In some embodiments, at least two of the droplets from the first plurality of droplets comprises the one or more first analytes in different concentrations, or comprise different buffer conditions. At least two of the droplets from the first plurality of droplets can comprise different one or more first analytes.

In some embodiments, the analyte comprises one or more of proteins, nucleic acids, lipids, carbohydrates, and cells, or a combination thereof. The one or more potential reaction partners can comprise one or more of proteins, nucleic acids, lipids, carbohydrates, cells, or a combination thereof. The analyte and/or the one or more potential reaction partners can comprise drugs, enzymes, antibodies, immunogens, antigens, metabolites, antibiotics, microbial cells, or a combination thereof. The one or more potential reaction partners of the analyte can comprise one or more potential substrates of an enzyme, and wherein the analyte comprises an enzyme. The enzyme can be capable of catalyzing one substrate of the one or more potential substrates to a product. The one or more potential reaction partners of the analyte can comprise one or more enzymes potentially capable of catalyzing a substrate to a product, and wherein the analyte comprises the substrate. One enzyme of the one or more enzymes potentially capable of catalyzing the substrate to the product can be capable of catalyzing the substrate to the product. The substrate can be a drug, and the enzyme can be capable of metabolizing the drug to the product.

Nanostructure-Initiator Mass Spectrometry

In some embodiments, the mass of analytes, for example the reaction product generated by incubating a sample or enzyme with a substrate (e.g., a drug) can be determined by nanostructure-initiator mass spectrometry (NIMS). NIMS is described in Northen et al., Nature 2007, 449, 1033-1036; Northen et al., Proc. Natl. Acad. Sci. USA 2008, 105, 3678-3683; U.S. Patent Application Publication Nos. 2008/0128608, 2018/0254177, and 2018/0269052; U.S. Pat. No. 10,240,180; which are herein fully incorporated by reference. Production of NIMS chips is described in detail in, for example, Woo et al., Nat. Protoc. 2008, 3, 1341-1349, which is herein fully incorporated by reference. The ratio of substrate-to-reaction product ions in the mass spectrum can be analyzed to determine the presence of the enzyme of interest in the sample.

A variety of apparatuses can be used in NIMS to measure the mass-to-charge ratio of the ionized target. For example, in several embodiments a time-of-flight mass analyzer is used for measuring the desorbed and ionized target. However, other non-limiting examples of mass analyzers that can be used include magnetic ion cyclotron resonance instruments, deflection instruments, and quadrupole mass analyzers.

Sample Deposition System

Disclosed herein include embodiments of a device (e.g., the device 100 described with reference to FIGS. 1A-1C). for screening for an enzyme substrate, for screening for an enzyme capable of catalyzing a substrate to a product, for screening analytes (such as enzymes and substrates), or for sample deposition on a mass spectrometry surface. In some embodiments, the system comprises an imaging device for optically identifying first analytes deposited onto the mass spectrometry surface. In some embodiments, the system comprises a mass spectrometer, such as a MALDI mass spectrometer.

EXAMPLE

Some aspects of the embodiments discussed above are disclosed in further detail in the following example, which are not in any way intended to limit the scope of the present disclosure.

Example

Coupling of Mass Spectrometry with Droplet Microfluidics

This example describes the coupling of mass spectrometry (MS) imaging (such as a matrix-free surface-based mass spectrometry imaging) based on, for example, nanostructure-initiator mass spectrometry (NIMS)) with droplet microfluidics for screening enzyme activities at a massive scale. Through picoliter droplet deposition on the NIMS surface, up to 100,000 metabolite analyses can be screened on a single microfluidic chip. Screening for hydrolytic enzymes against a glycan and a model drug is described herein.

Figure 1B:
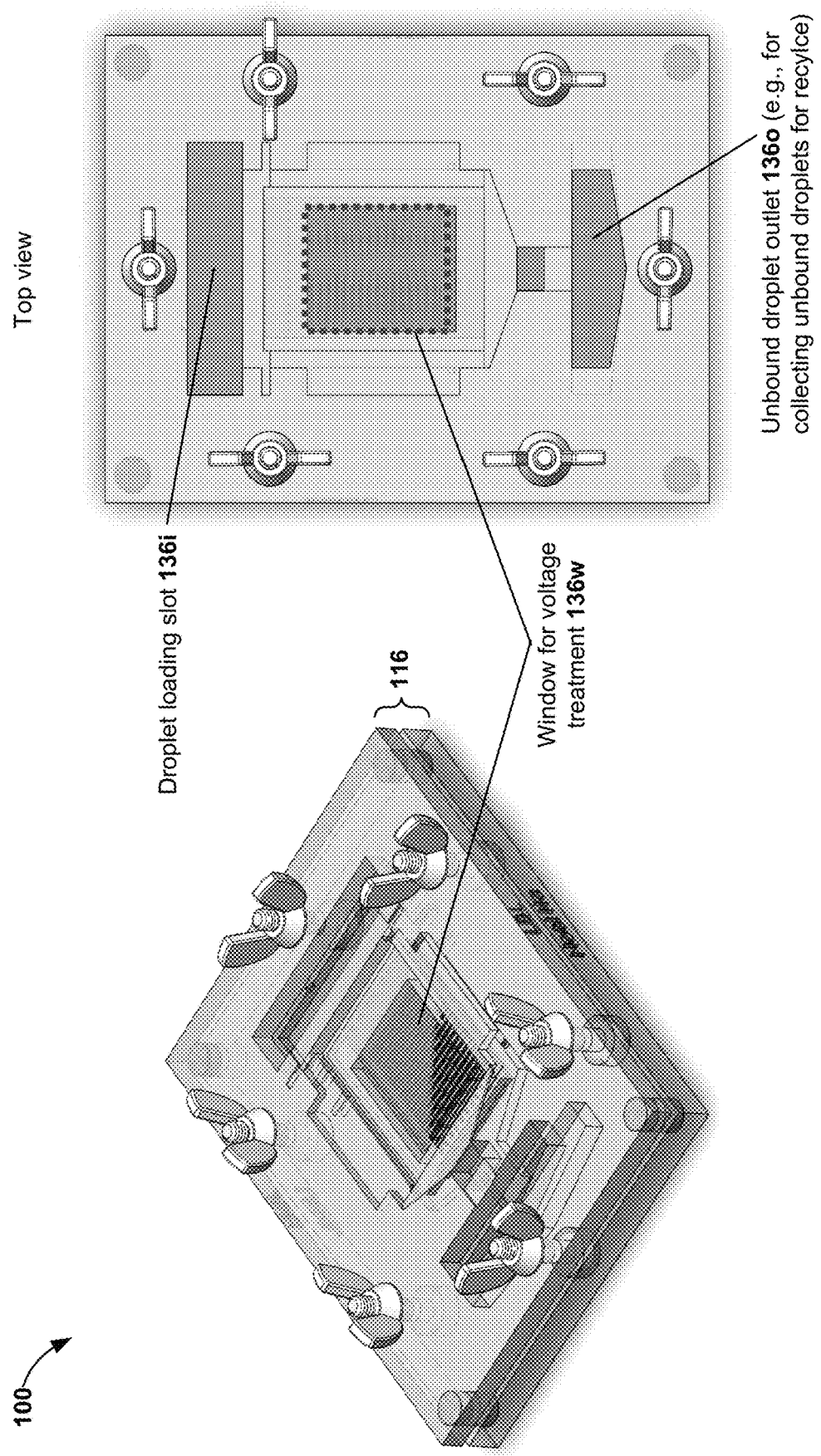
Figure 1C:
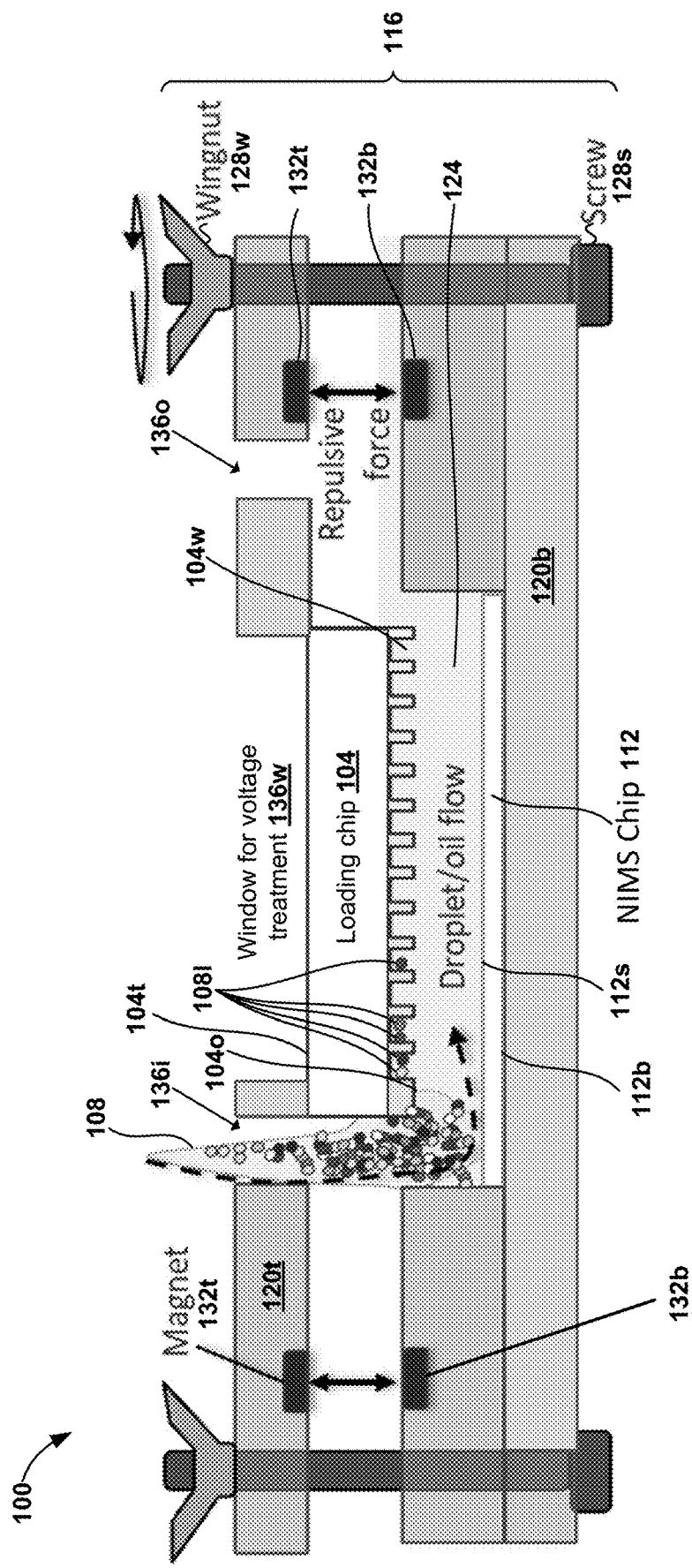
Figure 1D:
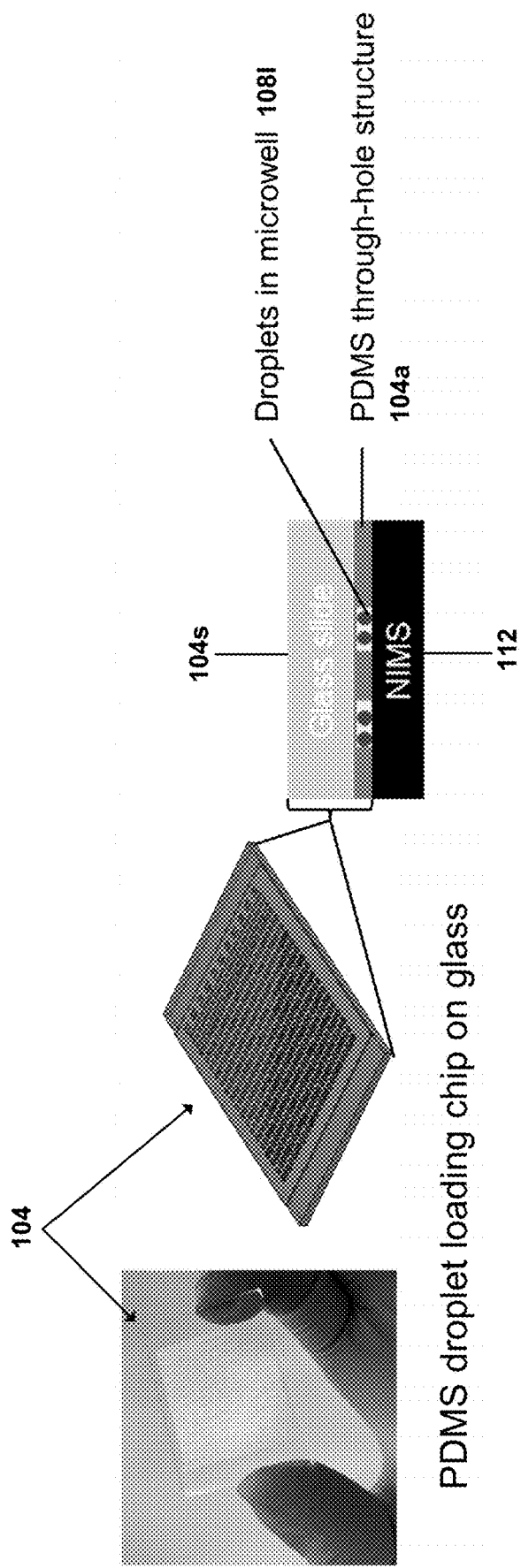
Figure 1E:
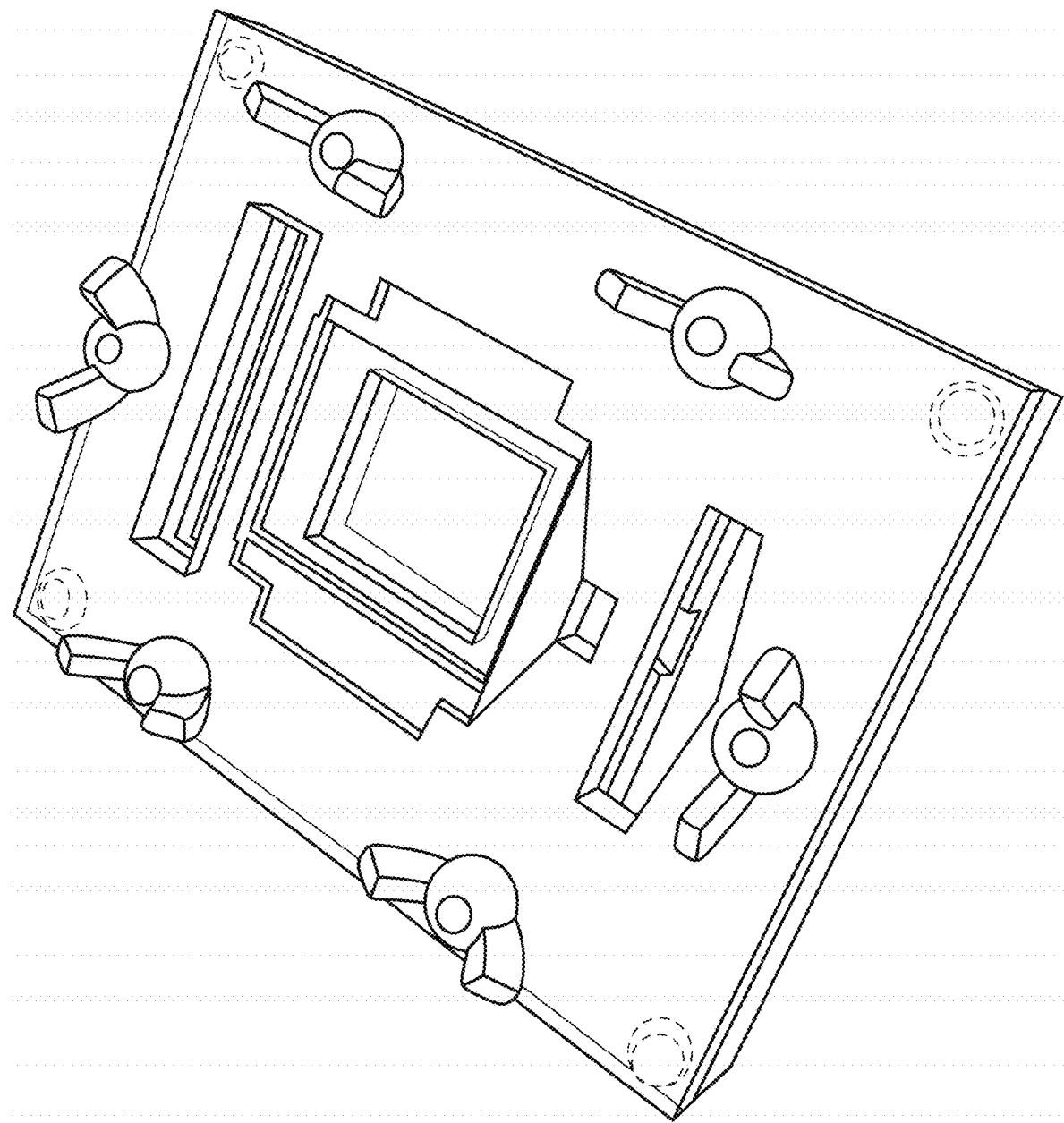
FIG. 1E is a non-limiting exemplary photograph of the droplet array generation apparatus without a loading chip.

A polydimethylsiloxane (PDMS)-on-glass microfluidic chip with an array of wells was fabricated for entrapment of picoliter droplets directly above a NIMS surface (FIGS. 1A-1E). Each well was ~145 µm in diameter to accommodate about 110 µm to 130 µm diameter droplet. A thinner PDMS layer on glass, instead of a bulky (~5 mm thick) PDMS-alone structure, was used. The PDMS layer was about 120-150 µm thick. The glass layer had a size of 25.4 mm (width)×40 mm (length)×1 mm (height). The top chip holder had a "window" for voltage treatment from top (FIGS. 1A-1C). Nylon screws and wingnuts were used to avoid electrical short circuits. The NIMS surface was prepared as previously described in Northen et al. (Nature 449, 1033-1036 (2007), the content of which is incorporated herein by reference in its entirety).

Single or double droplets were randomly trapped in the wells depending on the geometries of the wells, up to 100,000 droplets in a single-droplet design and 50,000 pairs in a double-droplet design. Two model substrates were chosen, including 1 mM drug Verapamil (455.30 m/z) and 1 mM cellobiose substrate with perfluorinated tail (G2-Ttag, 101.81 m/z). Droplets of about 110 µm diameter droplets were loaded and randomly trapped into the wells by the oil flow and droplet buoyancy (FIG. 2A). After the completion of droplet loading, the PDMS chip was sealed against the NIMS surface to confine droplets. For the double-droplet setup, the droplets in the wells were merged with a portable plasma treater for subsequent reaction. Volatile carrier oil evaporated through the gas-permeable PDMS top layer, resulting in deposition of contents of droplets via direct contact between droplet and NIMS surface. After complete evaporation, the NIMS surface was separated from the loading PDMS chip for mass spectrometry imaging (MSI) on a commercial MALDI MS (raster size 50 µm, FIGS. 3A-3B). On-chip droplet fluorescence imaging was then be performed on an automated plate imager for droplet identification and colorimetric assay (FIGS. 4I-4J).

Figure 5A:
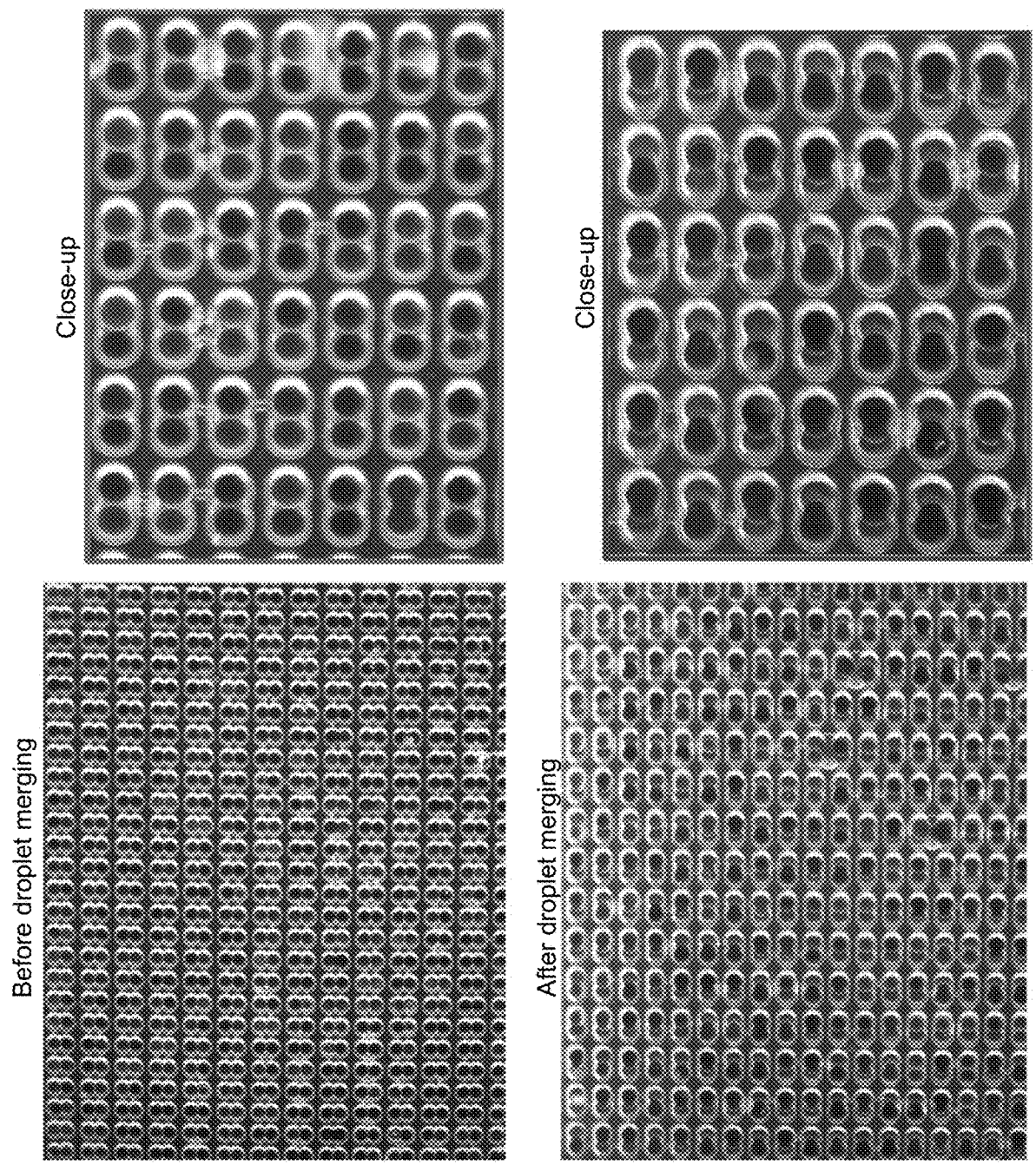
FIG. 5A shows non-limiting exemplary bright field images of a loading chip designed for loading two droplets into each well of a well array after droplet loading (top) and after (bottom) droplet merging.
Figure 5B:
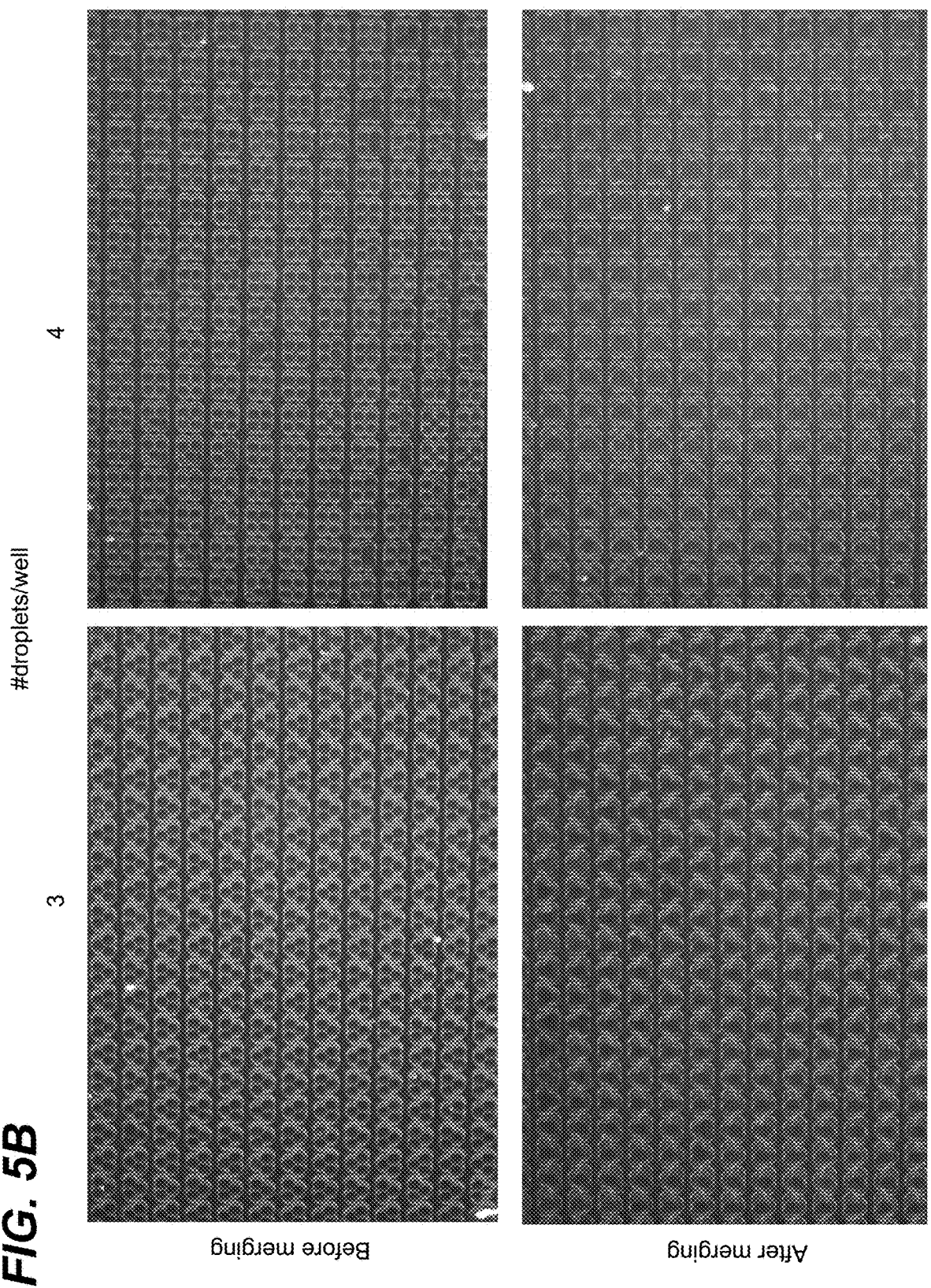
FIG. 5B shows non-limiting exemplary bright field images of loading chips designed for loading three droplets (left) and four droplets (right) into each well of a well array after droplet loading (top) and after (bottom) droplet merging.

FIG. 5A shows non-limiting exemplary bright field images of a loading chip designed for loading two droplets into each well of a well array after droplet loading (top) and after (bottom) droplet merging. FIG. 5B shows non-limiting exemplary bright field images of loading chips designed for loading three droplets (left) and four droplets (right) into each well of a well array after droplet loading (top) and after (bottom) droplet merging. AC voltage was applied through the top window and to the droplet loading chip, not to the mass spectrometry chip, to merge the droplets in wells.

Figure 6A:
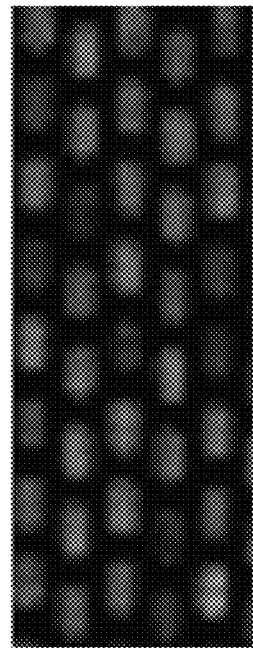
FIGS. 6A-6B show representative total ion content mass spectrometry images and mass spectra (marked with arrows) of deposited sample on NIMS surfaces.
Figure 6A:
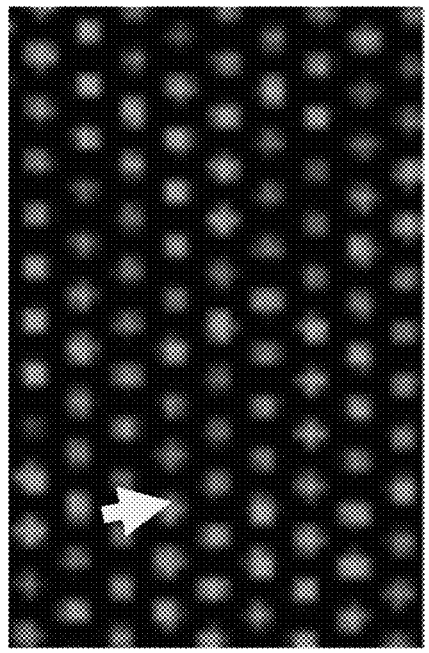
Figure 6A:
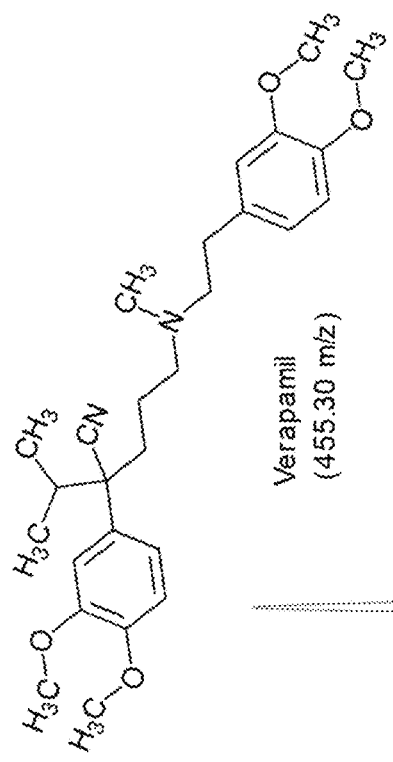
Figure 6A:
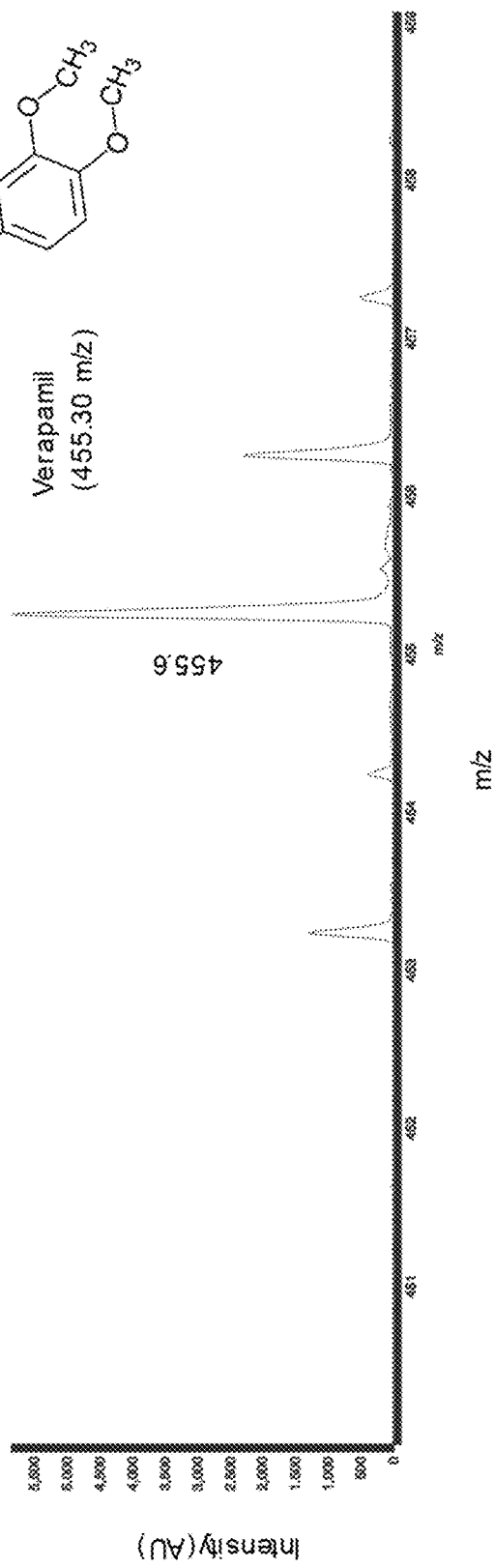
Figure 6B:
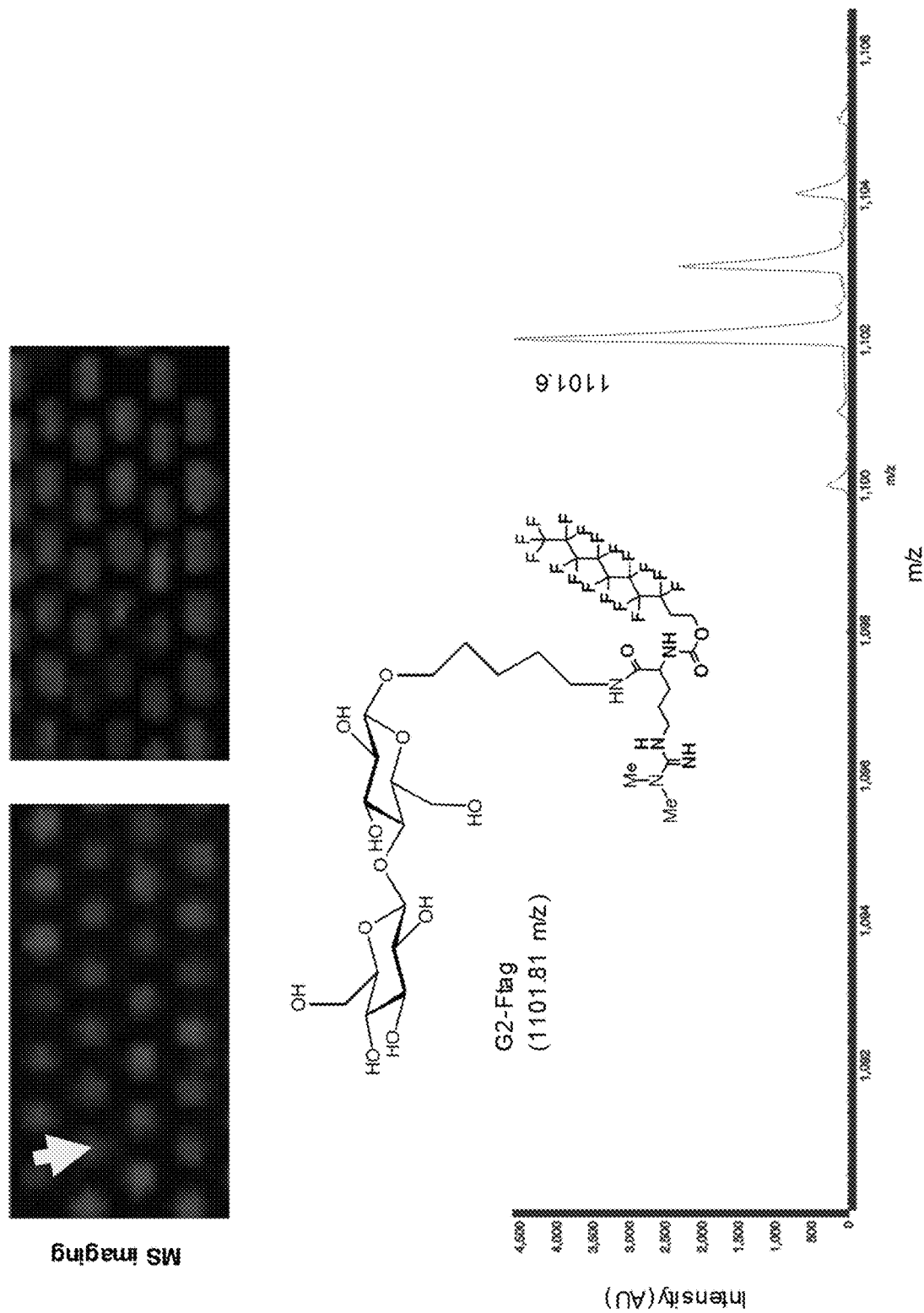

Buoyancy-based rapid droplet loading followed by sample deposition via evaporation of carrier oil was confirmed using MSI. MSI revealed successful deposition of both Verapamil and G2-Ttag and high signal-to-noise mass spectrometry results without interference from the carrier oil or solvent (FIGS. 6A-6B). Furthermore, no sample leakage from the wells was observed, demonstrating complete local confinement of sample without cross-contamination.

Figure 7A:
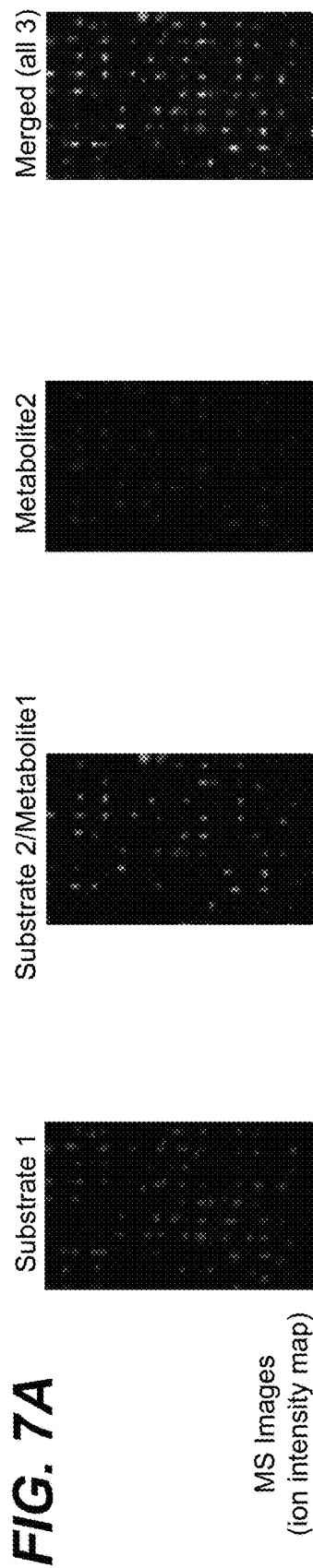
FIGS. 7A-7C show detection and monitoring of the droplet enzyme reaction (FIG. 7B) from G2-Ftag (cellobiose, first substrate) to G1-Ftag (first metabolite/second substrate) to Ftag (second metabolite) by CellECC-CBM3*a* using a device for sample deposition on a mass spectrometry surface disclosed herein.
Figure 7B:
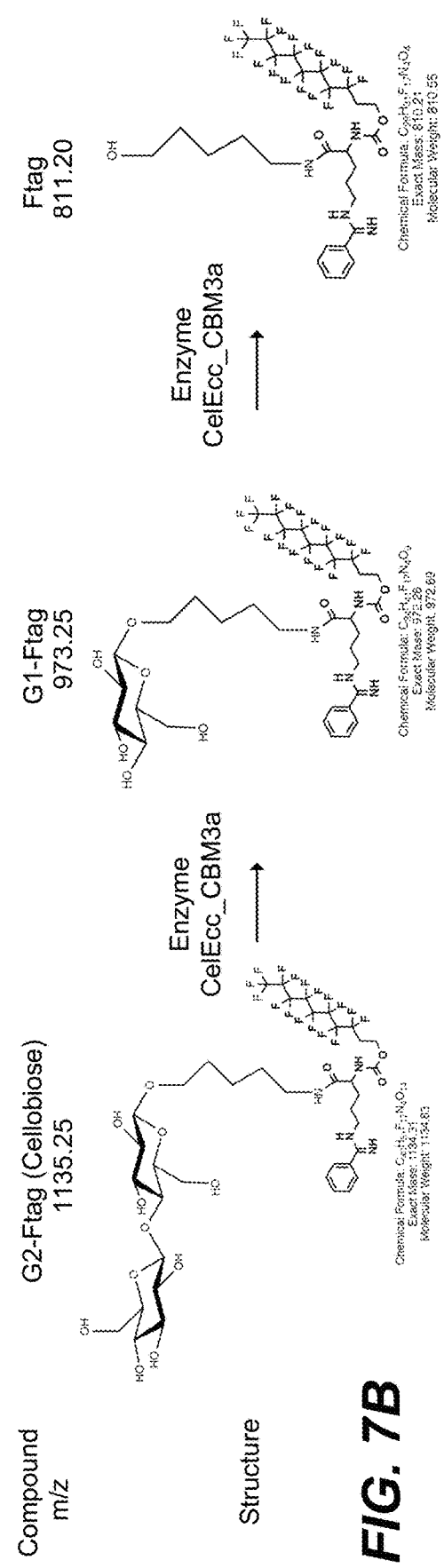
Figure 7C:
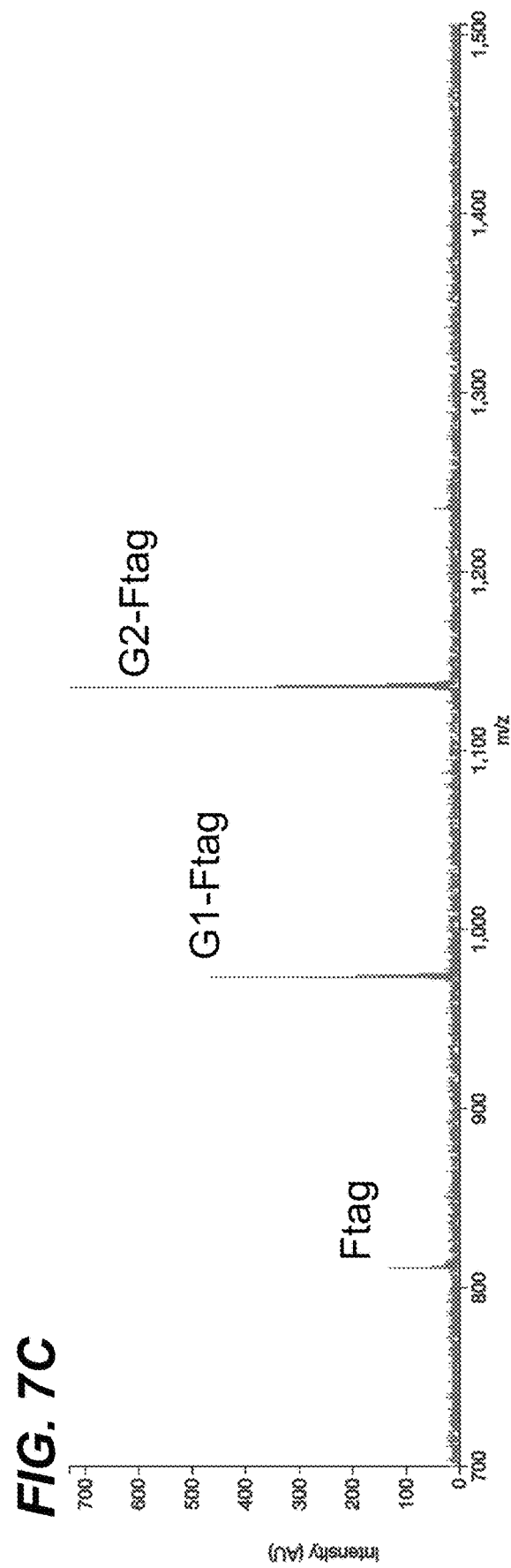

FIGS. 7A-7C show detection and monitoring of the droplet enzyme reaction (FIG. 7B) from G2-Ftag (cellobiose, first substrate) to G1-Ftag (first metabolite/second substrate) to Ftag (second metabolite) by CelECC-CBM3a using a device for sample deposition on a mass spectrometry surface disclosed herein. An enzyme droplet was merged with a substrate droplet for reaction. Successful detection of substrate and its metabolites were deposited onto NIMS (Mass spectrometry surface). Model biomass substrate (Cellobiose) and glycoside hydrolase enzyme (CelECC_CBM3a) were used. FIG. 7A shows non-limiting exemplary ion intensity maps of G2-Ftag, G1-Ftag, and Ftag. Each spot in the ion intensity map shows the quantity of G2-Ftag, G1-Ftag, or Ftag in a well as detected by MS. FIG. 7C shows a non-limiting exemplary MS spectrum showing all three components (G2-Ftag, G1-Ftag, and Ftag) in a well.

FIGS. 8A-8C show deposition and detection of mass spectrometry barcodes in droplets which can be used as sample identifiers. Each droplet contained one of five lanthanide barcodes. Each of the five lanthanide barcodes comprised a lanthanide chelator in complex with a different lanthanide metal. Lanthanide barcodes have been described in US 2017/0348665, the content of which is incorporated herein by reference in its entirety. The droplet loading chip used could hold two droplets per well, and each well of a loading chip can be used to load up to two lanthanide barcodes onto the MS surface. FIG. 8B shows ion intensity maps of each lanthanide barcode (2500 um×2500 um images 40 um step size raster). FIG. 8C shows merged ion intensity maps of three lanthanide barcodes, illustrating that each well of the loading chip loaded up to two lanthanide barcodes onto the MS surface.

This example demonstrates that the microfluidic approach described can enable rapid array construction and reaction directly above MS surfaces and be used for high-throughput combinatorial screening of enzymatic activity against substrate libraries to investigate important enzyme classes. The method comprises sample deposition onto nanostructured surface via oil evaporation. The chip design is flexible to accommodate more droplets per site, enabling investigation of multiple enzyme/substrate combinations as well as analysis of synergistic interactions and multi-step metabolic pathways. This platform can be used in discovery of new enzymes to support synthetic biology and bioenergy production as well as drug development.

Terminology

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. As used in this specification and the appended claims, the singular forms "a," "an," and "the" include plural references unless the context clearly dictates otherwise. Any reference to "or" herein is intended to encompass "and/or" unless otherwise stated.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method for screening analytes, comprising:
   (a) generating a first plurality of droplets each comprising one or more first analytes and a second plurality of droplets each comprising one or more second analytes;
   (b) distributing droplets from the first plurality of droplets and the second plurality of droplets onto an array of wells in a microfluidic device, thereby loading into one, at least one, or each, of the wells of the array zero, one, or two distributed droplets;
   (c) contacting a mass spectrometry (MS) surface of a mass spectrometry chip with a well-opening surface of the array of wells, thereby depositing (i) the one or more first analytes, or products thereof, if any, and (ii) the one or more second analytes, or products thereof, if any, from the zero, one, or two distributed droplets in the one, at least one, or each, of the plurality of wells onto a location on the mass spectrometry surface corresponding to the well;
   (d) obtaining a mass spectrum of the one or more first analytes, or products thereof, if any, and the one or more second analytes, or products thereof, if any, deposited onto one, at least one, or each, of the locations on the mass spectrometry surface; and
   (e) determining a first analyte and a second analyte are components of a reaction using a first peak, or absence thereof, corresponding to the first analyte, and/or a second peak, or absence thereof, corresponding to the second analyte in a mass spectrum of the mass spectra obtained.

2. The method of claim 1, wherein generating the first plurality of droplets comprises generating a droplet of the first plurality of droplets from a sample.

3. The method of claim 2, wherein the sample comprises a clinical sample, a soil sample, an air sample, an environmental sample, a cell culture sample, a bone marrow sample, a rainfall sample, a fallout sample, a sewage sample, a ground water sample, an abrasion sample, an archaeological sample, a food sample, a blood sample, a serum sample, a plasma sample, a urine sample, a stool sample, a semen sample, a lymphatic fluid sample, a cerebrospinal fluid sample, a nasopharyngeal wash sample, a sputum sample, a mouth swab sample, a throat swab sample, a nasal swab sample, a bronchoalveolar lavage sample, a bronchial secretion sample, a milk sample, an amniotic fluid sample, a biopsy sample, a cancer sample, a tumor sample, a tissue sample, a cell sample, a cell culture sample, a cell lysate sample, a virus culture sample, a nail sample, a hair sample, a skin sample, a forensic sample, an infection sample, a nosocomial infection sample, a production sample, a drug preparation sample, a biological molecule production sample, a protein preparation sample, a lipid preparation sample, a carbohydrate preparation sample, a space sample, an extraterrestrial sample or a combination thereof.

4. The method of claim 1, wherein the array of wells is positioned with the well-opening surface facing down, and wherein the mass spectrometry chip is positioned with mass spectrometry surface facing up.

5. The method of claim 1, wherein distributing the droplets from the first plurality of droplets onto the array of wells comprises flowing the first plurality of droplets in a carrier fluid through a channel formed by a space between the well-opening surface of the array of wells and the mass spectrometry surface, and wherein distributing the droplets from the second plurality of droplets onto the array of wells comprises flowing the second plurality of droplets in a carrier fluid through the channel formed by the space between the well-opening surface of the array of wells and the mass spectrometry surface.

6. The method of claim 1, further comprising: generating a mixture of the first plurality of droplets and the second plurality of droplets, wherein the droplets from the first plurality of droplets and the droplets form the second plurality of droplets are loaded into the array of wells together by distributing onto the array of wells the mixture of the first plurality of droplets and the second plurality of droplets.

7. The method of claim 1, wherein the droplets from the first plurality of droplets and the droplets form the second plurality of droplets are loaded into wells of the array of wells sequentially.

8. The method of claim 1, wherein one, at least one, or each, of the wells of the array is sized and/or shaped to capture
(i) at most one of the droplets from the first plurality of droplets, and
(ii) at most one of the droplets from the second plurality of droplets when the droplet from the first plurality of droplets is captured in the well of the array.

9. The method of claim 8, wherein the droplets from the first plurality of droplets are larger than the droplets from the second plurality of droplets, and wherein distributing the droplets from the first plurality of droplets occurs before distributing the droplets from the second plurality of droplets, thereby one, at least one, or each, of the wells of the array comprises: (i) none of the droplets from the first plurality of droplets and none of the droplets from the second plurality of droplets, (ii) one of the droplets from the first plurality of droplets and none of the droplets from the second plurality of droplets, (iii) one of the droplets from the first plurality of droplets and one of the droplets from the second plurality of droplets, or (iv) at least one of the droplets from the second plurality of droplets.

10. The method of claim 1, comprising merging one droplet from the first plurality of droplets and one droplet from the second plurality of droplets in the well where the two droplets are introduced into.

11. The method of claim 10, wherein merging the one droplet from the first plurality of droplets and the one droplet from the second plurality of droplets in the well where the two droplets are introduced into comprises applying a voltage.

12. The method of claim 11, wherein the side of the array of wells opposite of the well-opening surface of the array of wells is in contact with an additional layer, and wherein merging the one droplet from the first plurality of droplets and the one droplet from the second plurality of droplets in the well where the two droplets are introduced into comprises applying a voltage to the additional layer.

13. The method of claim 11, wherein merging the one droplet from the first plurality of droplets and the one droplet from the second plurality of droplets in the well where the two droplets are introduced into comprises applying a voltage to the mass spectrometry chip.

14. The method of claim 1, wherein contacting the well-opening surface of the array of wells with the mass spectrometry surface comprises sealing the well-opening surface of the array of wells with the mass spectrometry surface via a reversible sealing mechanism.

15. The method of claim 1, wherein the droplets from the first and/or second plurality of droplets rise or sink via buoyancy from the space between the well-opening surface of the array of wells and the mass spectrometry surface into the wells.

16. The method of claim 1, wherein distributing droplets from the first and/or second plurality of droplets comprises randomly distributing the droplets onto the array of wells.

17. The method of claim 1, wherein the one or more first analytes from the first plurality of droplets, the one or more second analytes from the second plurality of droplets, or both, comprise a protein, a polypeptide, a peptide, a nucleic acid, a lipid, a carbohydrate, a small molecule drug, a cell, or any combination thereof.

18. The method of claim 1, wherein the droplets from the first plurality of droplets, the droplets from the second plurality of droplets, or both are in a solvent-in-oil emulsion.

19. The method of claim 18, comprising evaporating the solvent, the oil, and/or the carrier fluid from the mass spectrometry surface.

20. The method of claim 1, wherein the droplets from the first plurality of droplets, the droplets from the second plurality of droplets, or both comprise a detectable barcode that identifies the one or more first or second analytes in a given droplet.

* * * * *